United States Patent
Sucholeiki

(10) Patent No.: US 6,277,332 B1
(45) Date of Patent: *Aug. 21, 2001

(54) REACTION PLENUM WITH MAGNETIC SEPARATION AND/OR ULTRASONIC AGITATION

(75) Inventor: Irving Sucholeiki, Watertown, MA (US)

(73) Assignee: Solid Phase Sciences Corporation, Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/049,245

(22) Filed: Mar. 27, 1998

Related U.S. Application Data

(63) Continuation-in-part of application No. 08/762,887, filed on Dec. 7, 1996, now Pat. No. 5,779,985.
(60) Provisional application No. 60/008,742, filed on Dec. 18, 1995.

(51) Int. Cl.[7] .............................. B01F 11/02; B06B 1/00; G01N 35/02
(52) U.S. Cl. .............................. 422/128; 422/20; 422/65; 422/127; 436/47; 366/116; 366/127
(58) Field of Search .............................. 422/20, 65, 104, 422/105, 109–111, 116, 127, 128, 67; 435/286.2, 286.4, 306.1, 308.1; 436/47, 49, 177; 366/127, 114, 113, 116; 134/184

(56) References Cited

U.S. PATENT DOCUMENTS 1,734,975 * 11/1929 Loomis .
3,301,535 * 1/1967 Brown .
3,325,976 * 6/1967 West .................................... 96/335

(List continued on next page.)

FOREIGN PATENT DOCUMENTS

WO 83/03920 11/1983 (EP) .
0 211 436 2/1987 (EP) .
WO 93/25912 12/1993 (EP) .

OTHER PUBLICATIONS

Timothy J. Mason, Practical Sonochemistry, User's Guide to Applications in Chemistry and Chemical Engineering, Ellis Horwood, London, ch. 2, pp. 56–59.
Sayomi Takahashi and Yasutsugu Shimonishi, Solid Phase Peptide Synthesis Using Ultrasonic Waves, Chemistry Letters, 1974, pp. 51–56, Chemical Society of Japan.
Treleaven, et al, Removal of Neuroblastoma Cells From Bone Marrow With Monoclonal Antibodies Conjugates to Magnetic Microspheres, The Lancet, Jan. 14, 1984, pp. 70–73.
Raji Padmanabhan, et al, Purification of Transiently Transfected Cells By Magnetic Affinity Cell Sorting. Analytical Biochemistry 170, 341–348, Academic Press, Inc., 1988, Bethesda, MD.
Jan G. Fjeld, et al. In Vivo Evaluation of Radio–labelled Antibodies With Antigen–Coated Polymer Particles in Diffusion Chambers, Journal of Immuno–logical Methods, 109, 1988, pp. 1–7 Elsevier Science Publishers, Amsterdam, The Netherlands.

(List continued on next page.)

*Primary Examiner*—Marian C. Knode
*Assistant Examiner*—Alexa A. Doroshenk
(74) *Attorney, Agent, or Firm*—Perkins, Smith & Cohen, LLP; Jacob N. Erlich; Jerry Cohen

(57) ABSTRACT

The inventive apparatus is comprised of a means for producing cavitation in a complex reaction mixture to enhance the yield of the selected reaction product, a means for controlling the temperature of the complex reaction mixture, especially during cavitation, and a means for affecting magnetic separation of paramagnetic beads to which the selected reaction product is attached from the complex reaction mixture. In one embodiment, the compound(s) or molecule(s) is synthesized in situ, and isolated using the inventive apparatus. The apparatus finds use in the fields of solid phase organic synthesis, and for isolation and purification of a selected compound(s) or molecule (s), especially where automation is desired.

32 Claims, 17 Drawing Sheets

U.S. PATENT DOCUMENTS

| | | |
|---|---|---|
| 3,552,536 | 1/1971 | Emary . |
| 3,811,623 | 5/1974 | Speer . |
| 3,837,805 | 9/1974 | Boucher . |
| 3,951,605 | 4/1976 | Natelson . |
| 4,022,579 | 5/1977 | Revillet et al. . |
| 4,259,290 | 3/1981 | Suovaniemi et al. . |
| 4,582,990 | 4/1986 | Stevens . |
| 4,919,807 | 4/1990 | Morton . |
| 4,973,876 * | 11/1990 | Roberts ................................ 310/316 |
| 5,176,446 * | 1/1993 | Chiba et al. ......................... 366/114 |
| 5,206,171 * | 4/1993 | Dillon et al. ......................... 435/293 |
| 5,380,487 | 1/1995 | Choperena et al. . |
| 5,413,770 * | 5/1995 | Sakaguchi et al. .................. 422/225 |
| 5,446,263 | 8/1995 | Eigen et al. . |
| 5,496,517 | 3/1996 | Pfost et al. . |
| 5,722,444 * | 3/1998 | Prokopenko et al. ............... 134/184 |
| 5,736,100 * | 4/1998 | Miyake et al. ......................... 422/64 |
| 5,779,985 * | 7/1998 | Sucholeiki .......................... 422/128 |

OTHER PUBLICATIONS

Stefan Miltenyi, et al, High Gradient Magnetic Cell Separation With MACS, Cytomery 11:231–238, 1990, Wiley–Liss, Inc., West Germany.

Kenneth S. Suslick, Sonochemistry, Science, vol. 24, pp. 1439–1445, Mar. 23, 1990, American Association For the Advancement of Science, USA.

Trevor L. Hawkins, et al, DNA Purification and Isolation Using a Solid–Phase, Nucleic Acids Re–search, vol. 22, No. 21 pp. 4543–4544, 1994, USA.

Diversomer 8–Pin Synthesizer, catalog, Chemglass, Vineland, New Jersey, USA, 1996.

* cited by examiner

REACTION PLENUM WITH MAGNETIC SEPARATION AND/OR ULTRASONIC AGITATION

CROSS-REFERENCE TO RELATED APPLICATIONS

This application is a continuation-in-part of U.S. patent application filed Dec. 7, 1996, Ser. No. 08/762,887, entitled A Reaction Plenum and A Method for Use and now U.S. Pat. No. 5,779,985 issued Jul. 14, 1998 which also claims priority of U.S. Provisional Application Serial No. 60/008,742 filed Dec. 18, 1995.

STATEMENT OF GOVERNMENT INTEREST

This invention was partially funded by the Government under a grant from the National Institute of Health. The Government has certain rights in portions of the invention.

FIELD OF THE INVENTION

The present invention relates generally to an apparatus and a method for using that apparatus for solid-phase synthesis of organic compounds, and, more particularly, to using paramagnetic beads in connection therewith. The apparatus also finds use in isolation and purification of a selected compound(s) or molecule(s) from a complex reaction mixture.

BACKGROUND OF THE INVENTION

Pharmaceutical companies are at present thinking of new ways of shortening the time involved in developing new drugs. One of these new ways is to introduce rapid throughput biological screening. Another way is to use combinatorial methods to produce large numbers of structurally different organic molecules such as peptides, nucleotides and non-peptide compounds for biological screening. In both cases some level of automation will be required in order to speed up the drug development process. Synthesis of compound libraries for biological testing has been routinely made through the use of solid phase organic chemistry. Solid phase organic synthesis allows for the quick separation of products from unreacted starting material as well as reagents and side-products that are not originally bound to the support.

Where only relatively small amounts of selected molecules are produced and where diversity of molecular structure is key for library generation of synthesized small molecules, yield of the selected molecules from the synthesis has been limited. Further, the currently utilized apparatus and methods are time-consuming. Solid-support recovery utilizing paramagnetic beads as the support system has been used for isolation and purification of biologically generated molecules. However, the industry also faces the problem of how to efficiently isolate and recover such biologically generated molecules to produce libraries for testing and sequencing. Thus, automation of the process(es) is further desired.

In the field of solid-supported organic synthesis, the physical separation of the support from the solubilized components of the solvent reaction mixture has primarily been accomplished by filtration using a glass or polymer filter. Although filtration has been the method of choice in both solid-phase peptide and nucleotide synthesis, limitations exist that warrant the development of new approaches. One such limitation is the difficulty of automating the simultaneous washing and filtration of hundreds of small scale solid-phase reaction supports. Use of a magnetic separation method instead of simple filtration would provide an advantage when separating reaction products from small reaction volumes.

However, the use of magnetic separation in the field of solid-supported organic chemistry has been slow in coming due to the instability exhibited by the currently available supports in organic solvents such as dimethylformamide and methylene chloride. Upon exposure to these solvents the typical polymer coated magnetic beads (also termed magnetic or paramagnetic particles) dissolve due to the low cross-linking of the polymer surface. Beads having highly cross-linked surfaces are known. For example, Ugelstad in PCT International Published Application WO83/03920, the disclosure of which is incorporated herein by reference, provides such polystyrene paramagnetic beads. Such highly cross-linked beads are more stable in these solvents and can withstand higher temperatures. However, due to the high degree of cross-linking of the surfaces of such beads less reactive area for chemical synthesis is present.

A field that has had some success in translating some of its techniques into automation is immunodiagnostics. Generally, an immunodiagnostic assay is run in a buffered aqueous solution. For example as taught by Fjeld, J. G; et. al. in volume 109, page 1 of the *Journal of Immunological Methods* (1988) and by Choperena, A.; et. al. in U.S. Pat. No. 5,380,487, the teachings of each of which are incorporated herein by reference, in a competitive immunoassay system, exposing reactant-bound paramagnetic beads to a magnetic field can be used to separate bound antigen from unbound antigen which then allows quantification of the bound reactant. Further, Choperna (ibid.) teaches automated immunodiagnostic assays combining immobilization of reactants on the paramagnetic particles during washings, and a fluid delivery means comprised of a pump and a probe having an ultrasonically activatable tip to dispense fluid. In addition to dispersing fluid into the vessel, the probe is inserted into the fluid and functions to mix the fluids and beads in the vessel, and to sense the fluid level in the vessel. To clean the probe after each use, the probe is removed from the fluid and the remaining liquid residue is atomized off of the tip. Dried contaminants potentially remain which can dissolve when the probe is next inserted into a liquid.

Utilizing paramagnetic beads having attached DNA for mixing buffered solutions containing a plurality of non-selected molecules is known. T. L. Hawkins, et. al. in *Nucleic Acids Research*, vol. 22, pp. 4543–4544 (1994), the teachings of which are incorporated herein by reference, teaches the use of paramagnetic beads for separation of selected DNA fragments from complex buffered fluid mixtures containing non-selected molecules. The buffered solutions are aspirated to remove the non-selected molecules, thus isolating and purifying DNA fragments from whole cells. Hawkins et. al. in PCT Int'l. Published Appl. WO93/25912 (1993), the disclosure of which is incorporated herein by reference, in addition to teaching the use of paramagnetic beads to immobilize a reactant while a complex fluid mixture is aspirated, teaches washing and stirring the paramagnetic beads having bound reactants by drawing the beads to one side through a wash medium using a magnet to drag the beads through the wash. Higo in EP 0 211 436, the disclosure of which is incorporated herein by reference, teaches of a magnetic stirrer which functions to move magnetic beads in a vessel by moving an external magnet proximal to the base of the vessel containing the magnetic beads.

Typically to obtain crude DNA, a solid-phase reversible immobilization or solid phase extraction procedure is used.

This involves lysating whole cells to obtain crude DNA and then binding this crude DNA to carboxylated paramagnetic beads in a reversible manner. Regarding this procedure, it is known that high energy ultrasonic waves can be used to disrupt or lysate cells. However, fully automated procedures for obtaining selected DNA or DNA fragments from lysated cells have not been perfected.

Magnetic separation methods have also been applied successfully in cell sorting as taught by J. G. Treleaven et. al. in *Lancet* vol. 14, p. 70 (1984); S. Miltenyi et. al. in *Cytometry*. vol. 11, p. 231 (1990); and R. Padmanabhan et. al. in *Analytical Biochemistry*, vol. 170, p. 341 (1988), the teachings of each of which are incorporated herein by reference.

K. S. Suslick in *Science*, vol. 247, p.1439 (1990), the teachings of which are incorporated herein by reference, has shown that high energy ultrasonic waves an enhance the reaction rates of certain chemical reactions. According to T. J. Mason in *Practical Sonochemistry, User's Guide to Applications in Chemistry and Chemical Engineering*, 1991, Ellis Horwood Limited, West Sussex, England, pp 46–48, the teachings of which are incorporated herein by reference, there are essentially four types of sonicating systems available. Of these, the most widely used are the "probe" and "bath" type. Probes are defined as having a transducer element which conducts ultrasonic energy to some horn made of titanium alloy which amplifies the ultrasonic energy. A bath type of sonicator is defined as a transducer element which is bonded to the bottom of a bath, sealed in a metal box which is immersed in the bath liquid (termed an "immersible sonicator"), or a transducer element protruding directly into the bath liquid. Although probe type sonicators which protrude from the bottom of a liquid filled bath or cup are sometimes categorized as "bath type sonicators," for the purposes of the present invention we shall term such "cup horn" type arrangements as also "probe" type sonicators. Takahashi and Shimonishi in *Chemistry Letters*, pp. 51–56 (1974), the teachings of which are incorporated herein by reference, have shown that insertion of an ultrasonic probe into a reaction mixture accelerated the rate of solid phase peptide couplings as well as aided in wash-out of molecules from resin. Again contamination as the probe is relocated from reaction mixture to reaction mixture remains a concern. Further, other problems are encountered when utilizing variable amplitude ultrasound in multiple parallel synthesis. Although commercially available ultrasonic probes produce ultrasonic waves of very high energy, the energy is not uniformly distributed over a wide area. While currently used ultrasonic baths, in contrast to ultrasonic probes, produce more uniform ultrasonic fields, they produce relatively weak ultrasonic energies as compared to probes.

A need exists for an automatic integrated machine for use with small fluid volumes which is capable of regulating the temperature of the reaction mixture during organic synthesis, of agitating the reaction mixture while reducing evaporative loss, and of magnetically separating paramagnetic particles from complex reaction mixtures in order to facilitate the use of paramagnetic particles in solid-phase organic synthesis. Further, a means for enhancing the rate of reaction during organic synthesis to increase efficiency and yield is wanted.

Improved methods of DNA isolation from cells are also needed.

SUMMARY OF INVENTION

It is therefore an object of this invention to provide an apparatus, termed herein a reaction plenum, which can facilitate the running of multiple simultaneous solid phase reactions as well as solid phase DNA extractions in small volumes of fluid which contain a plurality of reactants, herein termed a complex reaction mixture.

Another object of this invention is to provide a reaction plenum which can effectively mix and separate paramagnetic particles from complex reaction mixtures in a multiple array format.

A further object of this invention is to integrate the use of high energy, variable amplitude sonication and magnetic separation into one automated system to increase efficiency and/or yield of organic reactions.

In one aspect, the instant invention is an apparatus for organic synthesis of selected organic reaction products and isolation and purification thereof, which preferably is automated. The organic reaction products are produced and recovered in high yield with the use of a solid-phase paramagnetic bead support in a complex organic solvent mixture of reactants. The apparatus for organic synthesis in a vessel seated in a water bath, wherein the vessel contains a reaction mixture which has at least one solvent, at least one reactant, and at least one paramagnetic bead having a reactive site thereon, is comprised of a means for providing an ultrasonic field (also termed an ultrasonic means); a means for providing a magnetic force (also termed a magnetic force means) for immobilizing the paramagnetic beads; and a means for transporting the paramagnetic bead(s) in the solvent between exposure to the ultrasonic field and to the magnetic force. If desired, the beads could be stationary and the ultrasonic means and the magnetic means moved, but this would not usually be the preferable arrangement. In another aspect of the instant invention wherein temperature sensitive chemical reactions are run, there is a means for regulating the temperature of the water bath in addition to the aforementioned components.

In another aspect of the instant invention when synthesis of organic molecules of various chemical composition is desired, such as when building a library of molecules, a means for dispensing a volume of solvent (also termed a dispensing means) is provided, in addition to the ultrasonic means, the magnetic force means and the means for transporting. The dispensing means can provide at least one organic solvent containing at least one reactant into the vessel and/or a solvent wash into the vessel. In simplest form, a library of molecules is built by providing a paramagnetic bead with a reactive site, coupling a first small molecule such as a first amino acid or a first nucleotide to the paramagnetic support. A second reactant is coupled to the bound reactant. Where a plurality of beads are present in separate vessels, each vessel may receive a different second reactant. Such reactions and randomization of additions are then carried out until a plurality of reaction products are achieved with each vessel potentially having a unique bound reaction product. When building such a library, preferably the dispensing means is capable of dispensing a small volume of the solvent.

For some applications it is desirable to isolate the molecules bound to the paramagnetic beads. One such application is isolation and purification of a reaction product. Another application is recovery of DNA from cell lysates. For isolating a selected reaction product which is bound to a paramagnetic bead from a reaction mixture, the inventive apparatus comprised of an ultrasonic means, a magnetic force means, and a means of transporting, further includes a means for aspirating off a reaction mixture containing a non-selected reaction product(s). Preferably, the apparatus is provided with a water bath to facilitate control of the temperature of the reaction mixture. Where the solvent dispensed contains at least one reactant and generation of a library of molecules is desired, the inventive apparatus also includes a dispensing means.

When the inventive apparatus is used to isolate and purify products such as from a cell lysate solution, in a first embodiment, the apparatus is comprised of paramagnetic beads, an ultrasonic means, a magnetic means, and a means of transporting. Preferably, the paramagnetic beads are those taught by I. Sucholeiki, et. al. (U.S. patent application Ser. No. 08/585,905; filed Jan. 16, 1996 and now U.S. Pat. No. 5,834,121 issued Nov. 10, 1998), the disclosure of which is incorporated herein by reference. In a second embodiment, the apparatus comprises a means for dispensing a buffered solution containing cells onto a paramagnetic solid-phase support having a reactive site, an ultrasonic means, a means for providing a magnetic force for immobilizing the paramagnetic solid-phase support having a reactant thereon, and a means for aspirating the cell lysate mixture from contact with the paramagnetic bead(s) having the reactant coupled thereto. In this embodiment the ultrasonic means functions to lyse the cells as well as to facilitate mixing and washing. One example of a reactant which could be isolated from cells in this manner is DNA or a DNA fragment. Preferably, the apparatus includes a water bath to facilitate control of the temperature of the complex mixture of reactants. In both embodiments, the ultrasonic means advantageously increases yield of the desired component or reactant when used in accordance with the present invention.

In an embodiment of the apparatus for organic synthesis, the means for transporting includes a stepper motor which provides for slow acceleration and deceleration of the vessel holding the paramagnetic solid-phase support bead(s) and a reaction mixture, and a means for connecting the stepper motor to the vessel in which a reaction occurs. Such means for connecting can include, although it is not limited to, a screw drive, a belt drive, a rod-gear-sprocket combination, or a cord and pulley mechanism.

A method of use of the apparatus for organic synthesis includes: providing at least one paramagnetic bead with a reactive site; dispensing a small volume of at least one reactant in at least one organic solvent, termed a reaction mixture, onto the paramagnetic bead; exposing the paramagnetic bead and reactant in solvent to an ultrasonic field to thereby produce cavitation bubbles for a length of time sufficient to enhance the reaction rate between the reaction site on the paramagnetic bead and the reactant and thereby producing a bound reaction product; mobilizing the paramagnetic beads in a magnetic field to affect isolation of the bound reactant. Preferably, isolation of the bound reactant also includes the step of aspirating the reaction mixture away from the magnetically immobilized paramagnetic beads.

In one embodiment of the inventive apparatus, the means for transporting the paramagnetic beads in the solvent between the means for providing a magnetic force and the means for providing a substantially uniform ultrasonic field is comprised of: a solvent stable reaction vessel support means; a reaction vessel; and a means for transporting the reaction vessel. Preferably, the means for transporting minimizes movement of the solvent, also termed sloshing of the solvent. In an example of the means for transporting, a reaction plate holder is provided to support the reaction plate, in which at least one reaction vessel is seated, essentially at the water level of a water bath that is capable of providing a temperature controlled environment. A first mounting block or a number of first mounting blocks depending upon the size of the reaction plate holder is seated on the reaction plate holder. The first mounting block has a hole sized to receive a supporting rod which preferably is threaded to make the rod screw-like. The supporting rod is rotatably attached to a motor, preferably by a connector. Preferably, the hole in the first mounting block is threaded, so that when the motor is activated, the supporting rod rotates causing the first mounting block by virtue of the threaded interior of the hole to move linearly above the water level of the bath. A second mounting block is attached to the reaction plate holder and is not threaded so that it acts primarily to guide the screw-like rod.

In a second embodiment of the means for transporting, a belt, gear, and a motor system are provided. Preferably, a stepper motor is used. In this embodiment, guide rods direct the plate when gears activated by the motor engage the belt.

A water bath is provided with a sonication region at its proximal end and a magnetic separation region at its distal end at the bottom of the bath. An inlet tube is provided at the proximal end of the water bath and an outlet tube is provided at the distal end of the water bath to allow free circulation of water through the bath. Preferably, a means to regulate the water temperature is provided. The reaction vessels are partially submerged in the water of the bath. In a preferred embodiment, a dispensing means is located proximal to the sonication region and an aspiration means is located proximal to the magnetic separation region.

The reaction vessels may have rounded bottoms or may have flat bottoms. Preferably, the vessels have flat bottoms and are conical in shape having inwardly sloping walls extending from the bottom of the vessel.

In one embodiment of the reaction vessel holder, a means for providing an inert atmosphere within the reaction vessels is present.

For organic syntheses, at least one reactant in solvent is added to a reaction vessel which also contains at least one paramagnetic bead having a reactive site. The contents of the reaction vessel are sonicated resulting in a paramagnetic bead having a reactant covalently bound to its reactive site. The motor is activated thus advancing the reaction plate holder with the reaction plate(s) and reaction vessel(s) towards the magnetic separation region. The magnetic separation is activated causing the paramagnetic bead(s) and the attached reaction product to be retained in the reaction vessel. The solvent and remaining reactants are aspirated from the reaction vessel, leaving the reaction product attached to the paramagnetic bead. The reaction product is then cleaved from the paramagnetic bead. If desired, the paramagnetic bead may be washed where appropriate. Further, the steps of addition of reactant(s), sonication, and magnetic separation an be repeated until the desired reaction product is attained. Then, the reaction product is cleaved from the paramagnetic bead. The reactants added at each step are dependent upon the desired reaction product structure desired.

The instant invention is an apparatus, termed a reaction plenum, for isolation and/or organic synthesis of selected organic products and for purification thereof or for isolation and purification of selected organic compounds only. Preferably, the reaction plenum is automated. In one aspect, the reaction plenum is used for organic synthesis in a reaction vessel containing an organic solvent, a reactant and a paramagnetic solid phase support such as a paramagnetic bead having a reactive site. In this aspect the reaction plenum is comprised of a means for providing an ultrasonic field wherein the source of the ultrasonic field is exterior to the vessel (also termed an ultrasonic means), a means for providing a magnetic force for immobilizing the paramagnetic beads (also termed a magnetic force or field means), and a means for selectively, e.g., alternatively, exposing the reaction vessel to a magnetic field and to an ultrasonic field by exposing a reaction vessel to the means for providing a magnetic force and the means for providing an ultrasonic field when the reaction vessel is moved between them, there being means for providing such transport, and when the magnetic field and ultrasonic fields are moved there is means for providing this type of transport. Preferably, a means for dispensing a volume of solvent either containing a reactant for synthetic addition and/or a solvent wash is provided (also termed a dispensing means). Most preferably when the reaction plenum is utilized for generating a library of molecules, the amount of solvent dispensed is in the microliter range. Temperature control of the reaction mixture is also preferred. In one embodiment of the invention, the ability to maintain an inert atmosphere in the reaction vessel is provided.

The means for transporting has a number of components which can be varied according to the reaction or isolation conditions needed. A first embodiment of the means for transporting at least one reaction vessel is comprised of a means for mounting the reaction vessels in a water bath wherein the means for mounting can mechanically slide along a longitudinal plane which is substantially parallel to the surface of the water in a water bath; a drive mechanism; and a means for guiding the means for mounting in a water bath when the drive mechanism is activated. In a second embodiment, a means for providing an inert atmosphere to the reaction vessel is incorporated into the means for mounting.

The solid phase chemical reactions for which the reaction plenum can be used include general organic chemical reactions such as acetylations, alkylations, saponifications, metal mediated Stille couplings, Suzuki reactions, Mitsunobu reactions and reductive aminations. The reaction plenum is also useful for isolating DNA from cells. When low energy sonication is used, the reaction plenum can also be used to assist in the mixing and separation of solid phase biological assay reactions such as immunological, enzymatic and agglutination reactions. Several embodiments described will provide dimensions and reaction volumes for use in a small molecule drug discovery application wherein a plurality of small molecules having varying structure are synthesized to produce a molecular library of compounds. But the invention is not to be construed as particularly restricted to any of the cited examples or dimensions should the apparatus be used for larger scale synthesis or isolation and purification.

In a first embodiment of the ultrasonic means, the ultrasonic means functions to mix the magnetic beads having reaction sites in an organic synthesis reaction mixture which includes at least one solvent and at least one reactant using variable amplitude ultrasonic waves produced through a series of commercially available sonicating cup horns seated at one end in half of the water bath. The sonicating horns are externally located relative to the reaction vessels. While not wishing to be bound by theory, the sonicating cup horns are thought to enhance the reaction rate of solid phase organic chemical reactions by transferring energy from the horns, through the glass reaction vessels onto the surface, and into the cavities of the paramagnetic beads through cavitation. The energy of cavitation produced, then facilitates exchange of reactants at the reactive sites on the paramagnetic beads, provides highly localized heating, and facilitates deoxygenation of the reaction mixture.

In a first embodiment of the magnetic means, magnetic separation of the paramagnetic support is accomplished with a permanent magnetic field produced through a series of commercially available neodymium magnetic discs embedded in half of the water bath at the end opposite the sonicating cups. Upon activation of the motor and screw assembly which exemplify a first embodiment of the means for transporting, the plate holder carrying the four 96-well plates is caused to slide from the sonicating region where the sonication cups are located to the magnetic separating region where the neodymium magnetic disc arrays are located in the water bath.

Exposure to the magnetic fields results in immobilization of the paramagnetic beads at the vessel solvent interface. Insert of a means for aspiration solvent from the vessel results in isolation of the reaction product on the paramagnetic bead. At this point if desired, the reaction product may be further isolated and purified. Alternatively, paramagnetic bead with bound reaction may be utilized.

In one arrangement the reaction vessel is exposed only to sonication and computer control is provided for controlling the ultrasonic means by actuating and deactuating the ultrasonic means and for controlling the amplitude and duration of the ultrasonic field of the ultrasonic means.

Other objects, features and advantages will be apparent from the following detailed description of preferred embodiments, taken in conjunction with the accompanying drawings in which:

DETAILED DESCRIPTION OF PREFERRED EMBODIMENTS

A first embodiment of the present invention will be described referring to the accompanying drawings.

Figure 1A:
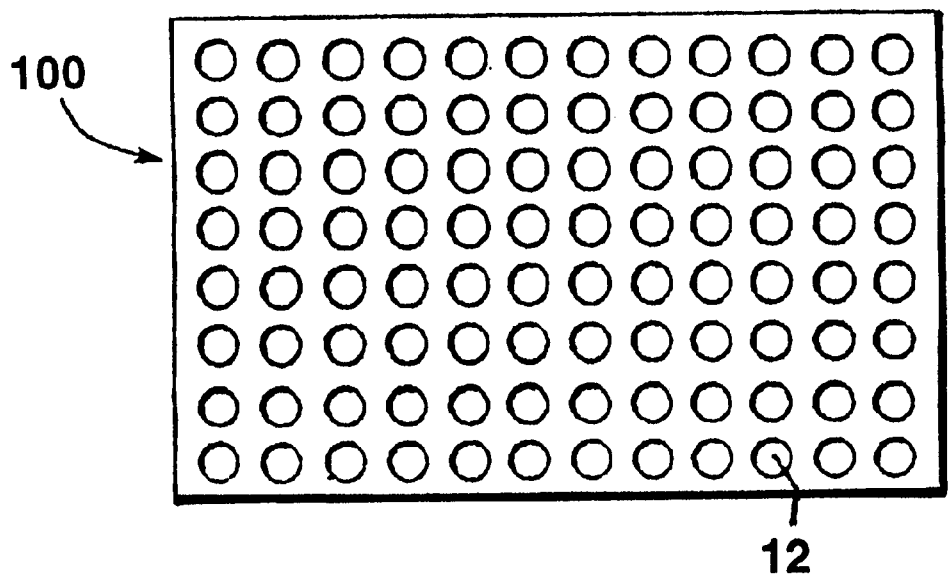
FIG. 1A is a schematic plan view of a means for holding the paramagnetic beads in a reaction vessel holder or reaction plate.

Referring now to FIG. 1A which shows a first embodiment of a reaction plate, the reaction plate (this embodiment of a reaction plate generally referenced in FIGS. 1A–6B as 100 when shown) is made of an organic solvent stable material such as polypropylene. Its dimensions are approximately 3¼ inches by 4$^{15}\!/_{16}$ inches in this embodiment. Each reaction plate has wells 12 sized to retain reaction vessels 14. The reaction plate 100 shown in FIG. 1A has 96 wells 12 drilled therein. Each well 12 has a reaction vessel which can be a glass or Pyrex reaction vessel 14 in the form of a tube, 1⅓–3 inches long and ⅛–⅜ inches wide, seated therein. The reaction vessel tubes 14 are inserted in such a manner that their bottoms pass through the reaction plate wells and extend at least ¼ inch or more into the water bath (generally referenced when shown as 200 in FIGS. 3A–6B) at its closed end.

Figure 1B:
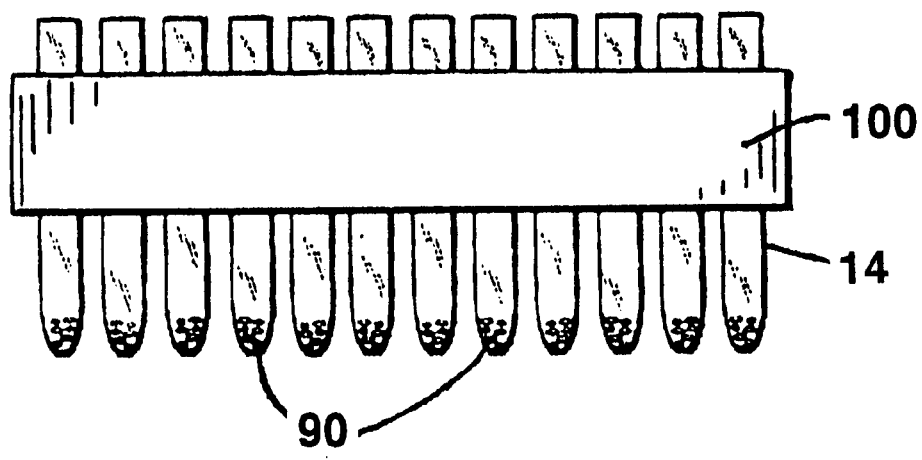
FIG. 1B is a schematic side view of the reaction plate of FIG. 1A which illustrates the positioning of reaction vessels in the reaction plate.

Referring now to FIG. 1B which shows the reaction plate 100 with reaction vessels seated therein, a series of reaction vessels each containing one or more paramagnetic beads 90 is illustrated. A plurality of paramagnetic beads is preferred. The paramagnetic beads 90 to be placed in each reaction vessel 14 include polystyrene based paramagnetic beads, silica based paramagnetic beads and others.

Paramagnetic beads that can be used with the instant invention include, for example, those described in U.S. Pat. Nos. 4,554,088 (Whitehead, et al.) which discloses paramagnetic particles comprising a metal oxide core surrounded by a coat of polymeric silane; U.S. Pat. No. 5,356,713 (Charmot), which discloses a magnetizable microsphere comprised of a core of magnetizable particles surrounded by a shell of a hydrophobic vinylaromatic monomer; U.S. Pat. No. 5,395,688 (Wang) which discloses a polymer core which has been coated with a mixed paramagnetic metal oxide-polymer layer, the disclosure of each of which is incorporated herein by reference.

Also useful is another paramagnetic bead which utilizes a polymer core to adsorb metal oxide such as, for example, in U.S. Pat. No. 4,774, 265 (Ugelstad), the disclosure of which is incorporated herein by reference. Most preferably, paramagnetic beads having a plurality of primary beads or particles, each of which is a polymer coated or polymer encapsulated metal oxide which has inducible magnetic properties encapsulated in a mesh or matrix comprised of a thermoplastic polymer resin such as disclosed in I. Sucholeiki, et. al.(U.S. patent application Ser. No. 08/585, 905; filed Jan. 16, 1996and now U.S. Pat. No. 5,834,121 issued Nov. 10, 1998), are used. Preferably, the paramagnetic beads each have at least one reactive site attached thereto or can be treated to provide a reaction site. Useful reaction sites for the instant application include a plurality of aminomethyl sites or a plurality of Rink linker sites. Means of providing such sites are exemplified in I. Sucholeiki (U.S. patent application Ser. No. 08/462,2012; filed Jun. 5, 1995 and now U.S. Pat. No. 5,684,130 issued Nov. 4, 1997), the disclosure of which is incorporated herein by reference. Other useful paramagnetic beads having characteristics similar to the above paramagnetic beads with reaction sites or that can be caused to possess reaction sites are known to those skilled in the art.

Figure 2A:
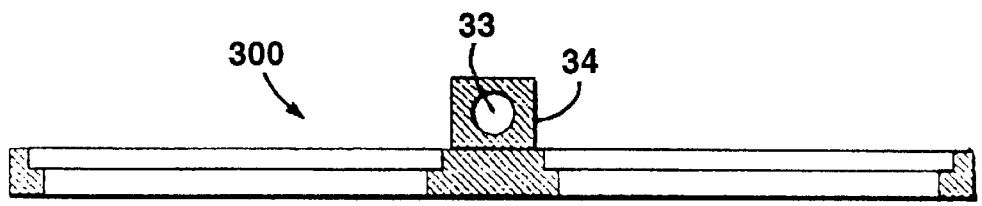
FIG. 2A is a cross-sectional side view taken generally along the plane defined by reference line 2A—2A of FIG. 2B of another aspect of the first embodiment of a means for transporting the paramagnetic beads, which is a reaction plate holder at a mounting block.
Figure 2B:
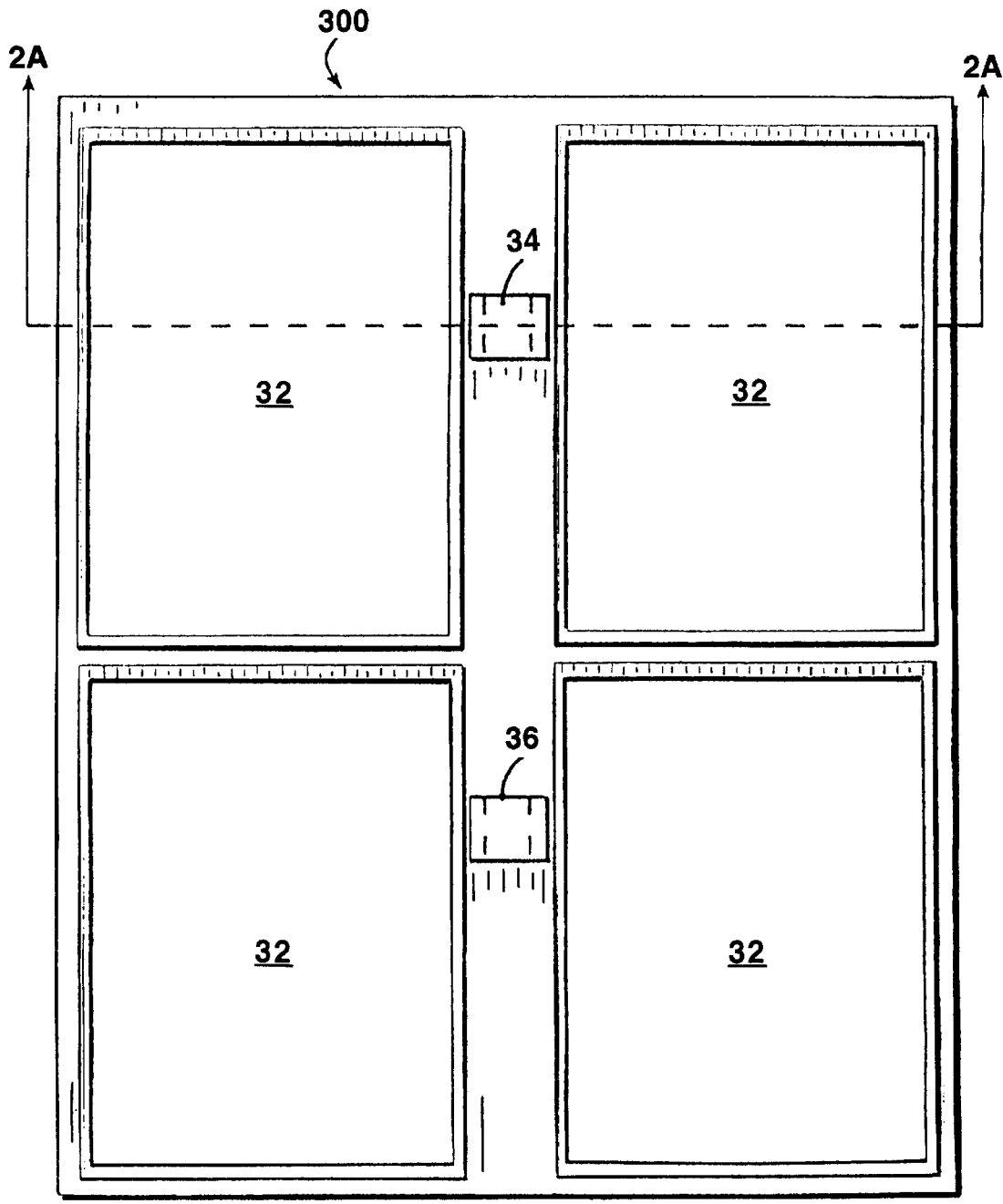
FIG. 2B is a plan view of the plate holder for the reaction plates shown in FIG. 2B.

Referring now to FIGS. 2A and 2B, this first embodiment of a reaction plate holder is generally referenced in all drawings as 300. The reaction plate holder 300 is about 12 inches in width and 23 inches in length for this application. It is made of ¼ inch thick acrylic. The reaction plate holder 300 can accommodate up to four 96-well reaction plates 100. Each reaction plate 100 is inserted into one opening 32 of the four square cut openings shown in the reaction plate holder 300. In FIG. 2A, seated and firmly attached at the top of the plate holder is a first square mounting block 34. FIG. 2B illustrates the placement of a first mounting block 34 and a second mounting block 36. Each mounting block is placed between two square cut openings 32 in the reaction plate holder. Each mounting block is approximately a ½ inch cube made of Delrin, an acetal (DuPont; Wilmington, Del.).

The first mounting block 34 is provided with a threaded hole 33 having approximately 13 threads/inch. The second block 36 contains a non-threaded ½ inch diameter hole. The second block 36 is used primarily to guide the screw (generally referenced as 40 in subsequent drawings). The first block 34 acts as a screw nut. Collectively, the two mounting blocks and the screw function as a means for transporting the reaction vessel. Manual or automated rotation of the crew causes the reaction plate holder 300, the reaction plate 100 and a vessel 14 seated therein to move longitudinally. The direction of rotation of the threaded screw determines the direction of transport of the vessel.

Figure 3A:
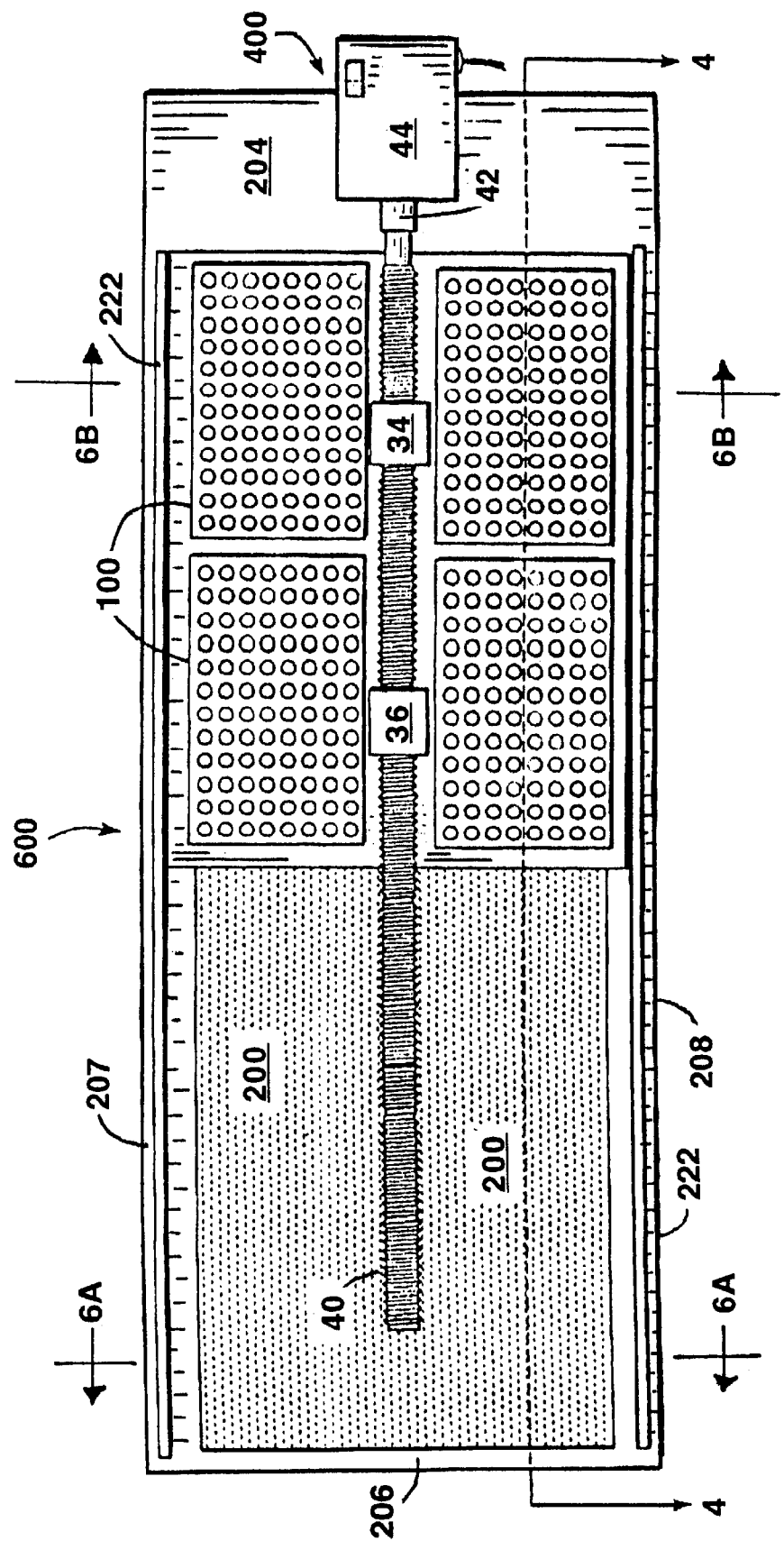
FIG. 3A is a schematic plan view of a reaction plenum having a plate holder with reaction plates and a motor driven screw seated over a water bath.
Figure 3B:
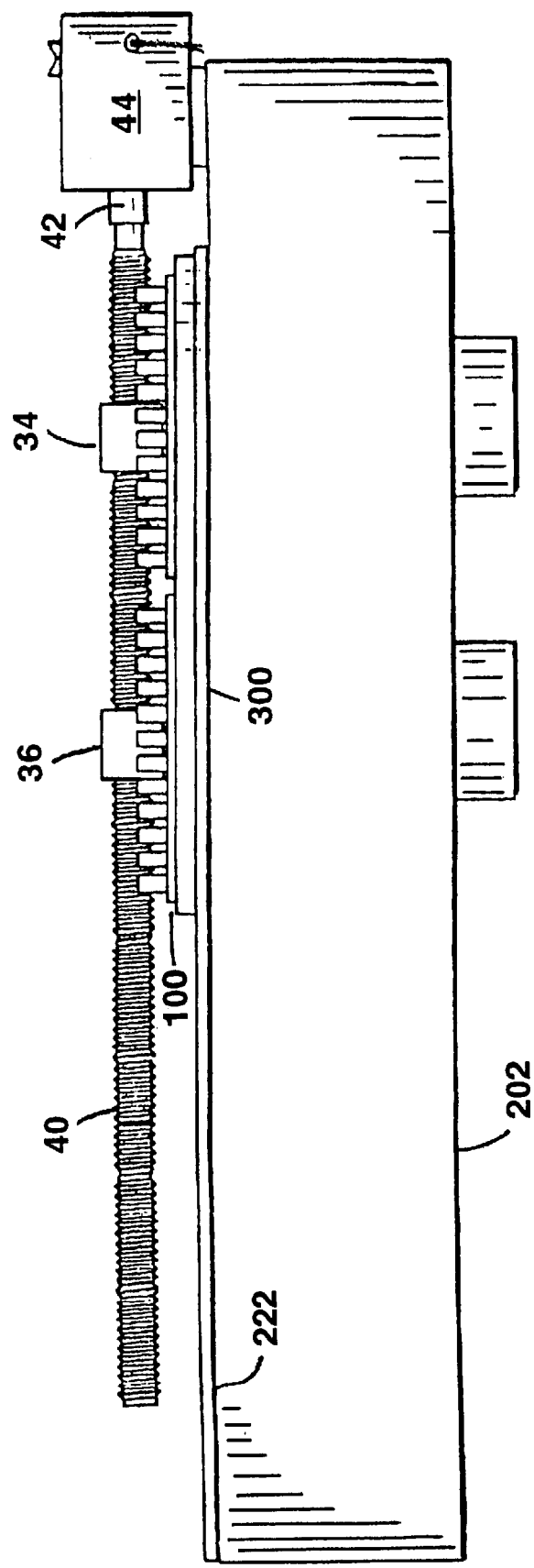
FIG. 3B is a schematic side view of the reaction plenum of FIG. 3A.
Figure 4:
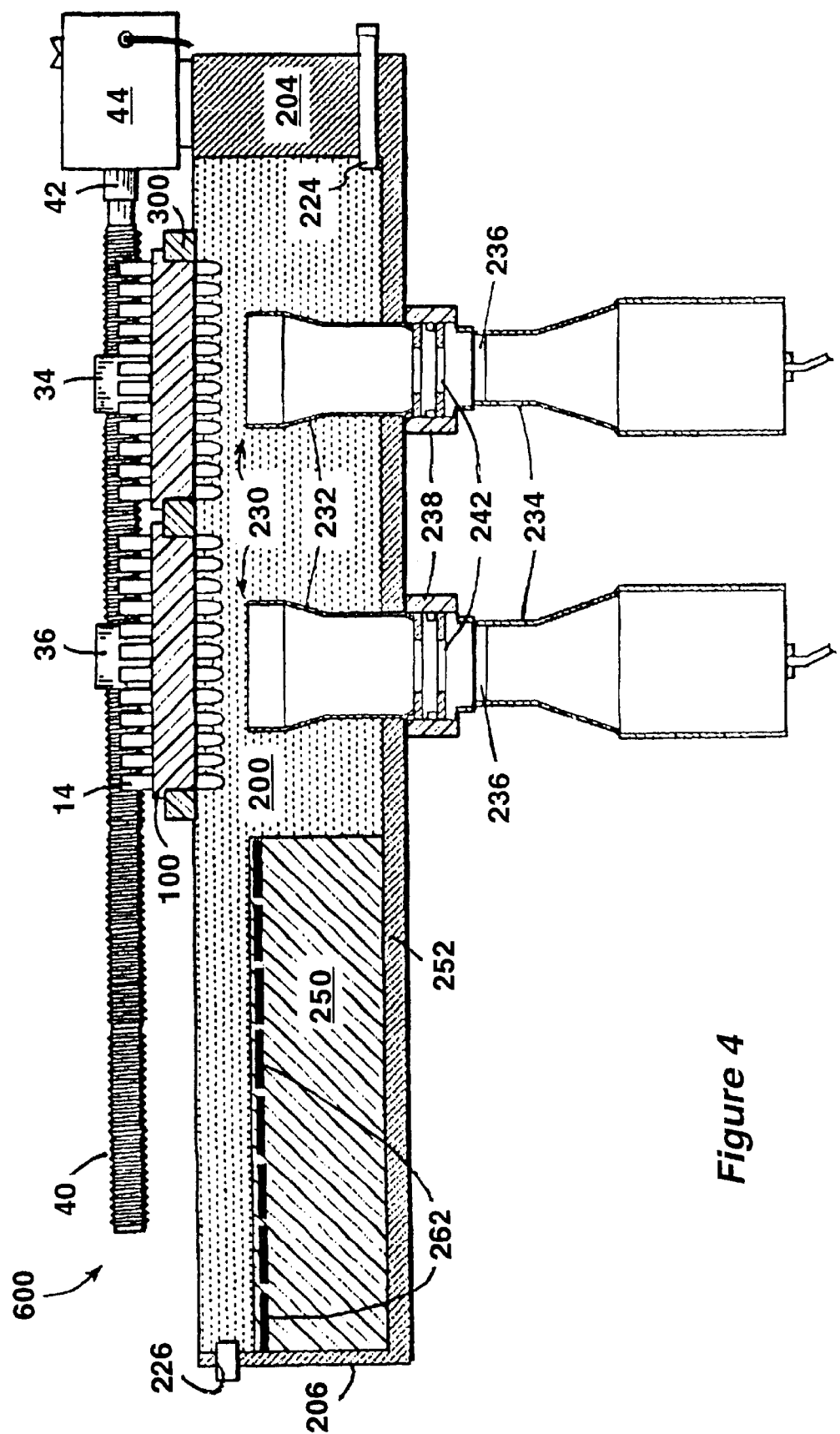
FIG. 4 is a cross-sectional side view of the reaction plenum of FIG. 3A and taken generally along the plane defined by reference line 4—4 of FIG. 3A.

Referring now to FIGS. 3A and 3B, the reaction plenum 600 is comprised of four 96-well reaction plates 100, the reaction plate holder 300, a screw 40, a motor assembly (generally referenced as 400) which is operably connected to the screw 40, and the water bath 200 which has an ultrasonication means (not shown) and a magnetic force means (not shown) positioned therein. The water bath 200 is essentially an open box having a bottom 202, a thickened proximal end 204 for supporting a motor, a thinner distal end 206, and two side walls 207 and 208, respectively. Each side wall has a slide guard 222 positioned along its length. The screw 40 is approximately 26 inches long and approximately ¼ to ½ inch in diameter with approximately 13 threads/inch. The screw 40 is attached to a metal coupling 42 (⁵⁄₁₆ inch ID). The coupling 42 is attached to a Clifton Precision 30 Volt DC motor 44. The motor 44 is powered by a 100–240 volt AC 60 cycles power supply with an AC Adapter and a 13.5 volt DC (2.0 amp) output. Upon activating the motor 44 clockwise or counter-clockwise, the screw 40 is made to turn which causes the reaction plate holder 100 to slide back and forth depending on the direction of the rotation of the screw 40. FIG. 4 illustrates the reaction plenum 600. The water bath distal wall 206, side walls and bottom are made of approximately ¼ inch thick acrylic panels, all of which are bolted together with the proximal end to form the open box. Each seam is water-proofed using sealant. The water bath may also be solvent sealed and/or vacuum drawn. The water bath 200 has inserted at its proximal end an inlet port 224 and at its distal end, an outlet port 226 to allow the free flow of water. The sonication region 230 of the water bath is composed of about one to four commercially available Misonix's brand (Farmingdale, N.Y.) sonicating cup horns. Each cup horn 232 has a radiating face diameter of 2.5 inches (550 watts) and protrudes through the bottom of the water bath 200. To each sonicating cup horn 232 is attached a separate 20 KHz converter 234, also known as a transducer, which is held in place using clamps 236. Each sonicating cup horn protrudes through an approximately ¼ inch thick acrylic ring 238 containing two 3 inch-in-diameter O-rings 242. The acrylic rings are sealed to the bottom of the water bath 200. Collectively, the sonicating horn and the 20 kHz converter comprise the ultrasonication means which can be used both for mixing when operated at low power and for enhancement of yield when operated at a power which results in substantial cavitation. While not wishing to be bound by theory, activation of the ultrasonic means in the presence of a solvent mixture in the reaction vessel is thought to result in cavitation bubbles. The energy of cavitation produced as the bubbles implode with continuing ultrasonification, is thought to then facilitate exchange of reactants at the reactive sites on the paramagnetic beads, provide highly localized heating, and facilitate deoxygenation of the reaction mixture. The magnetic separation region or magnetic force means (generally referenced in this first embodiment as 250) is composed of an acrylic box 252 which is approximately 11 inches in length, 8.5 inches in width and 2.5 inches deep. The acrylic box 252 is fixedly attached to the bottom of the water bath 200. Embedded in and spread out along the entire top of the box are arrays of commercially available approximately ½ inch diameter neodymium magnetic discs 262 (Master Magnetics, Inc.; Castle Rock, Colo.). In the first embodiment of the means for transporting, there is motor 44 which is positioned proximal to one end of the water bath, outside the interior of the water bath 200 itself; the screw 40 which extends substantially parallel to the surface of the water 202 in the water bath 200 from the motor 44 towards the opposite end of the water bath 200; and the plate holder in which reaction plates for supporting vessels are seated. The screw 40 supports and positions the reaction plate holder 100 above the water bath 200 at about the water level between the slide guards 222.

Figure 5:
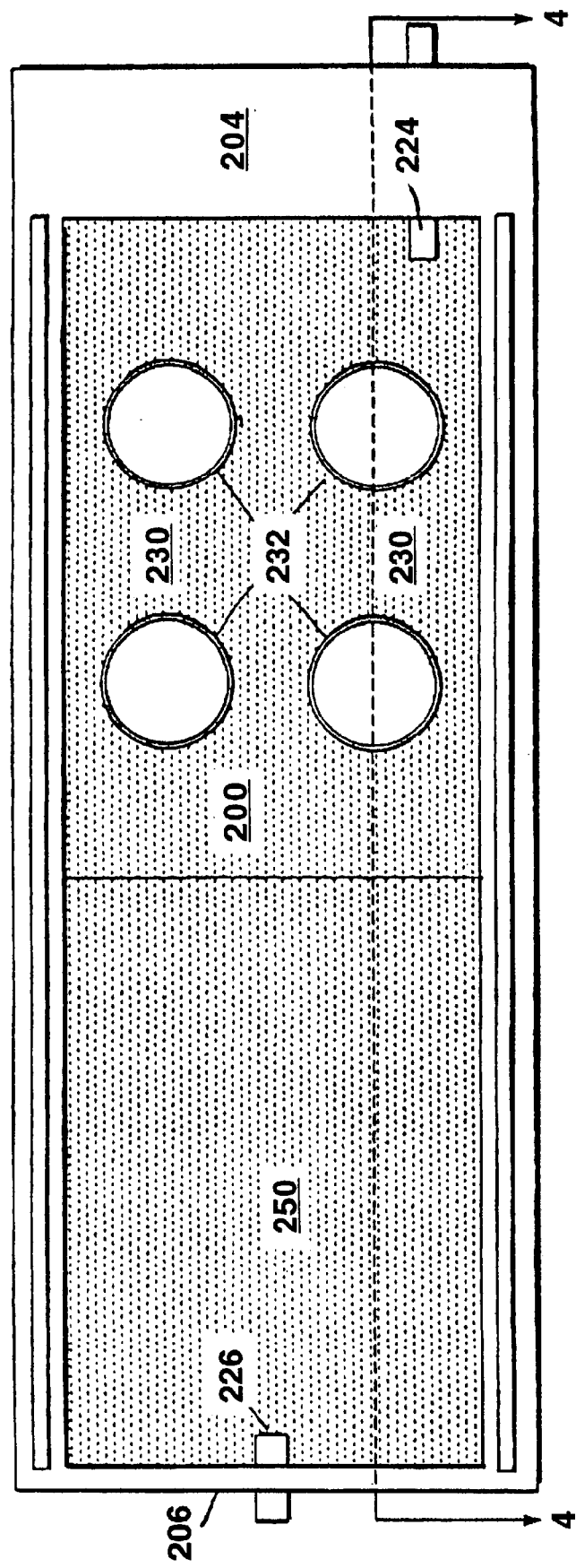
FIG. 5 is a view of the bottom of the water bath of FIG. 3A.

FIG. 5 is a plan view of the water bath 200 indicating the positioning of the ultrasonicating means which in this first embodiment thereof is exemplified by the four Misonix's brand sonicating cup horns 232 in the sonicating region 230 at the water bath bottom. A water inlet port 224 is shown protruding through the proximal wall 204 adjacent to the sonicating region 230. A water outlet port 226 is shown positioned in the distal wall 206 of the water bath proximal to the magnetic separation region 250.

Figure 6B:
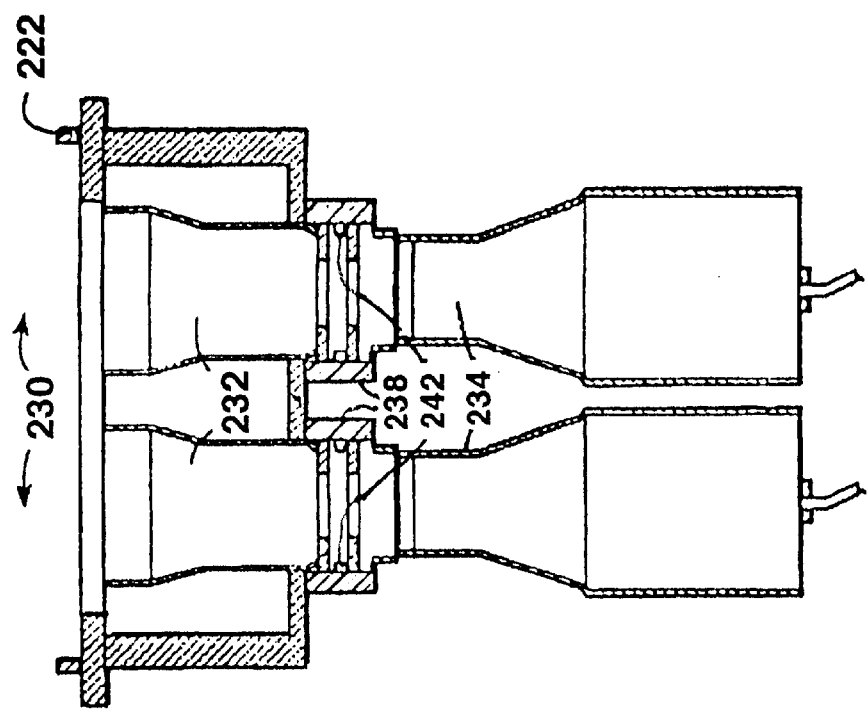
FIG. 6B is a cross-sectional end view of the sonication region of the reaction plenum taken generally along the plane defined by reference line 6B—6B of FIG. 3A.
Figure 6A:
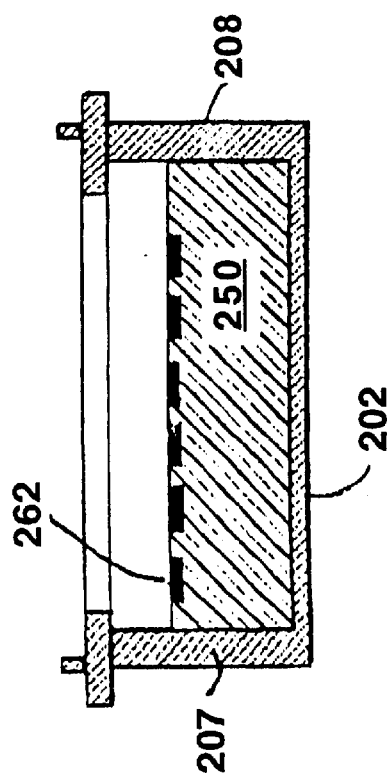
FIG. 6A is a cross-sectional end view of the magnetic separation region of the reaction plenum taken generally along the plane defined by reference line 6A—6A of FIG. 3A.

Referring now to FIGS. 6A and 6B, FIG. 6A illustrates a cross-sectional view of the end of the water bath at the magnetic separation region of the reaction plenum and indicating the positioning of the neodymium magnetic discs 262 in the magnetic separation region relative to the side walls of the water bath. Slide guards 222 are shown positioned at the top end of the water bath walls and are separated one from the other by about 8.5 inches. In this embodiment of the means for transporting, the slide guards function to direct the motion of the reaction plate holder. In contrast, the walls of the bath are about 9.5 inches one from the other. The width of the water bath including the slide guards is about 15 inches. FIG. 6B illustrates a cross-sectional view of the first embodiment of the ultrasonication means, the illustrated sonication region includes sonicating cups 232, O-rings 242, acrylic rings for mounting the cups 238, and the converter 234. Also illustrated is the positioning of the components of the sonication region relative to the water bath walls as viewed at the end of the water bath opposite the magnetic separation region.

The variable amplitude, ultrasonic waves produced by the sonicating cup horns travel through the water and through the glass reaction vessels and to the paramagnetic beads within resulting in an enhancement of the reaction rate of a solid phase reaction and/or assisting in the mixing of the reaction mixture. This process can occur only when the reaction plate holder is positioned over the sonicating region of the bath. Upon activation of the motor, the plate holder moves longitudinally over to the area of the bath containing the neodymium magnetic arrays. Once positioned over these arrays, the magnetic particles become attracted to the bottom of the reaction vessels. This allows for the manual or automated removal of the solvent and the soluble components of the reaction mixture through suction. Upon reversing the rotation of the motor, the reaction plate holder can again longitudinally slide back over the sonication region of the water bath. The reaction plate and reaction plate holder may repeatedly slide back and forth between the ultrasonication means in the sonication region and the magnetic means in the magnetic separation region depending on the task to be performed. The reaction block may be used manually or can be automated. The preferred embodiment has the reaction block integrated with a commercially available x-y-z automated solvent delivery robot such as the two arm X-Y-Z Tecan Liquid Handling Robot or the one arm X-Y-Z Tecan Liquid Handling Robot (Research Triangle Park, N.C.).

Figure 7:
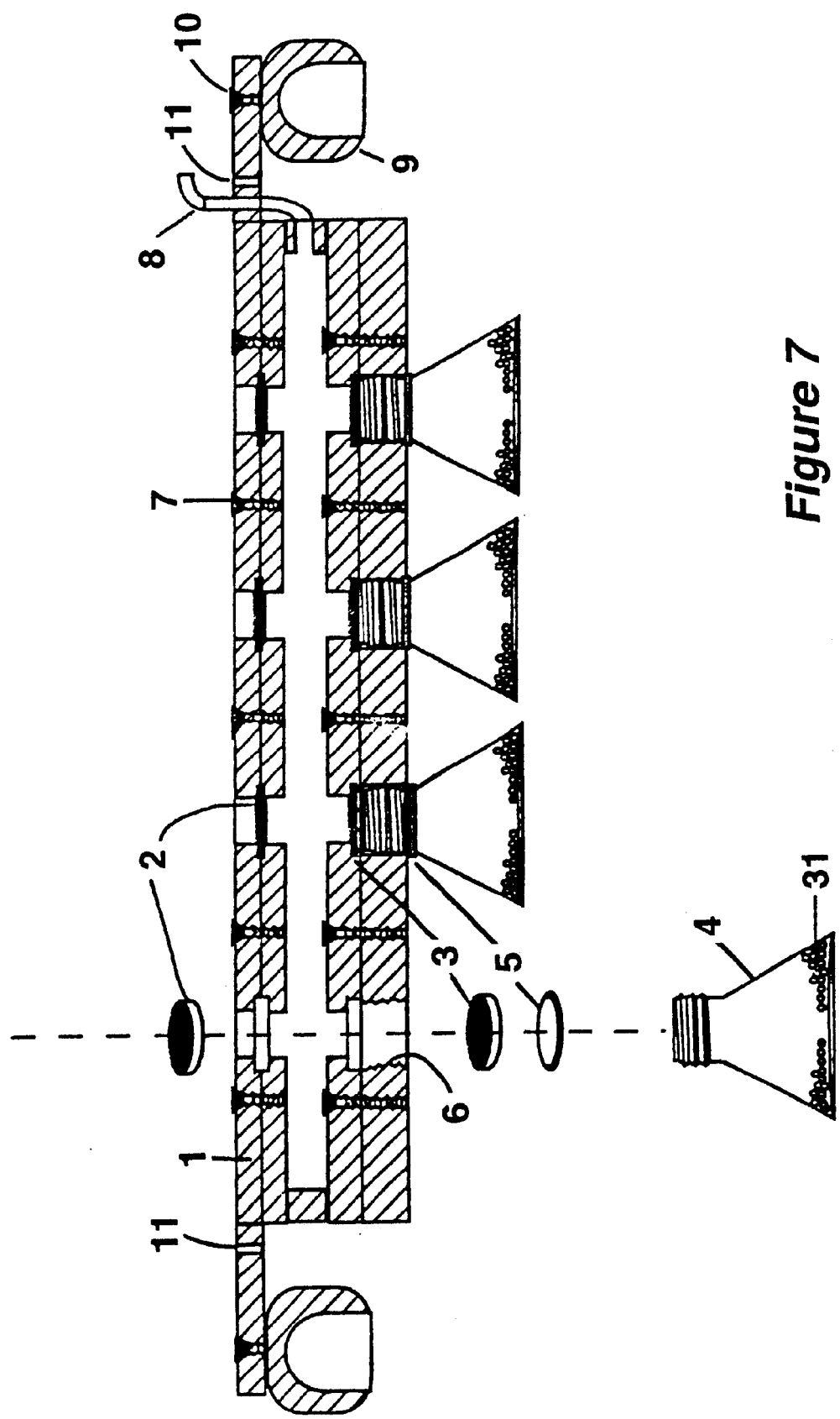
FIG. 7 is a cross-sectional side view of another embodiment of a reaction plate.

Referring now to FIG. 7, a schematic drawing of a second embodiment of the reaction plate is provided. In this embodiment, the reaction plate has a means for providing an inert atmosphere to the vessels. In this embodiment of the vessels, the vessels are conically shaped, flat bottomed flasks having a threaded neck for attachment to a threaded opening in the reaction plate. The presence of a means for providing an inert atmosphere is particularly useful for chemical reactions wherein oxidation is to be avoided. However, using of the illustrated reaction plate or the illustrated reaction vessel is not restricted to this particular embodiment of the reaction plenum. Other means of providing an inert atmosphere could be used, such as insertion of the reaction plenum into a hood which provides an inert atmosphere or insertion of individual septa, one septum per vessel with a needle used to provide the inert atmosphere. The described vessels are also useful with the above described first embodiment of the reaction plenum. While the desired Erlenmeyer flasks are preferred due to the surface area distribution, other reaction vessels such as flat bottomed vials or rounded bottom vials could be used. The vessels, be they vials, flasks or tubes, should be made of glass. Various combinations of reaction plate holders, reaction plates, drive mechanisms, and other components described can be arranged to suit the particular requirements of the reaction as will be exemplified below.

FIG. 7 shows a cross-sectional side view of the reaction plate 1 made up of 5 individual sheets of Teflon. Sandwiched between the top two sheets of Teflon are a series of rubber septa disks 2. Another set of rubber septa disks 3 are sandwiched between the bottom two sheets of Teflon. A series of threaded Erlenmeyer flasks 4 (obtained from Kontes, Vineland, N.J.) with a 5 ml volume capacity and fitted with Viton O-rings 5 are screwed in the bottom Teflon plate 6. All of the Teflon plates are held together with a series of threaded screws 7. A hole is bored through the side of the center Teflon plate and two plastic tubes 8 are attached parallel to each other. These tubes are used to circulate dry nitrogen or argon atmosphere through the plate. Two bearings 9 made of Delrin are attached to the underside of the top-most Teflon plate with a series of set screws 10. Four holes 11 are made through the top-most Teflon plate. These holes are used to lock the reaction plate 1 to the belt drive or track 21 using a series of metal pins. Polymer or silica coated paramagnetic beads 31 are placed in each Erlenmeyer flask 4.

Figure 8:
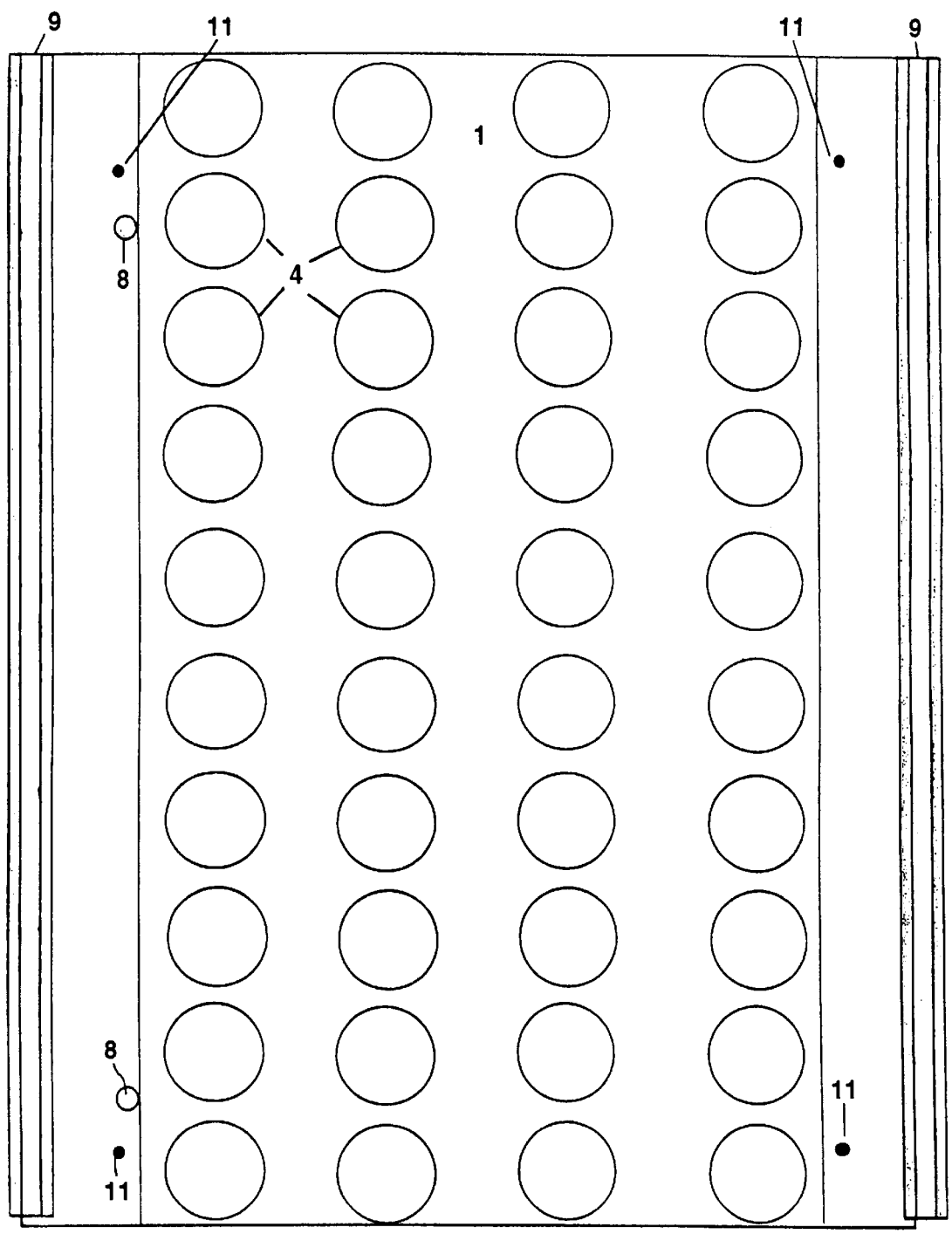
FIG. 8 is a view of the bottom of the reaction plate of FIG. 7.

Referring now to FIG. 8, a schematic drawing showing the bottom view of the Teflon reaction plate 1. The bottoms of the flasks 4 are arranged in a 4×10 matrix. The bottoms of the two bearings 9 are seen adjacent to the inert gas inlet and outlet tubes 8 and the track locking pin holes 11. The plate holder can accommodate up to forty 5 ml flasks 4.

Figure 9:
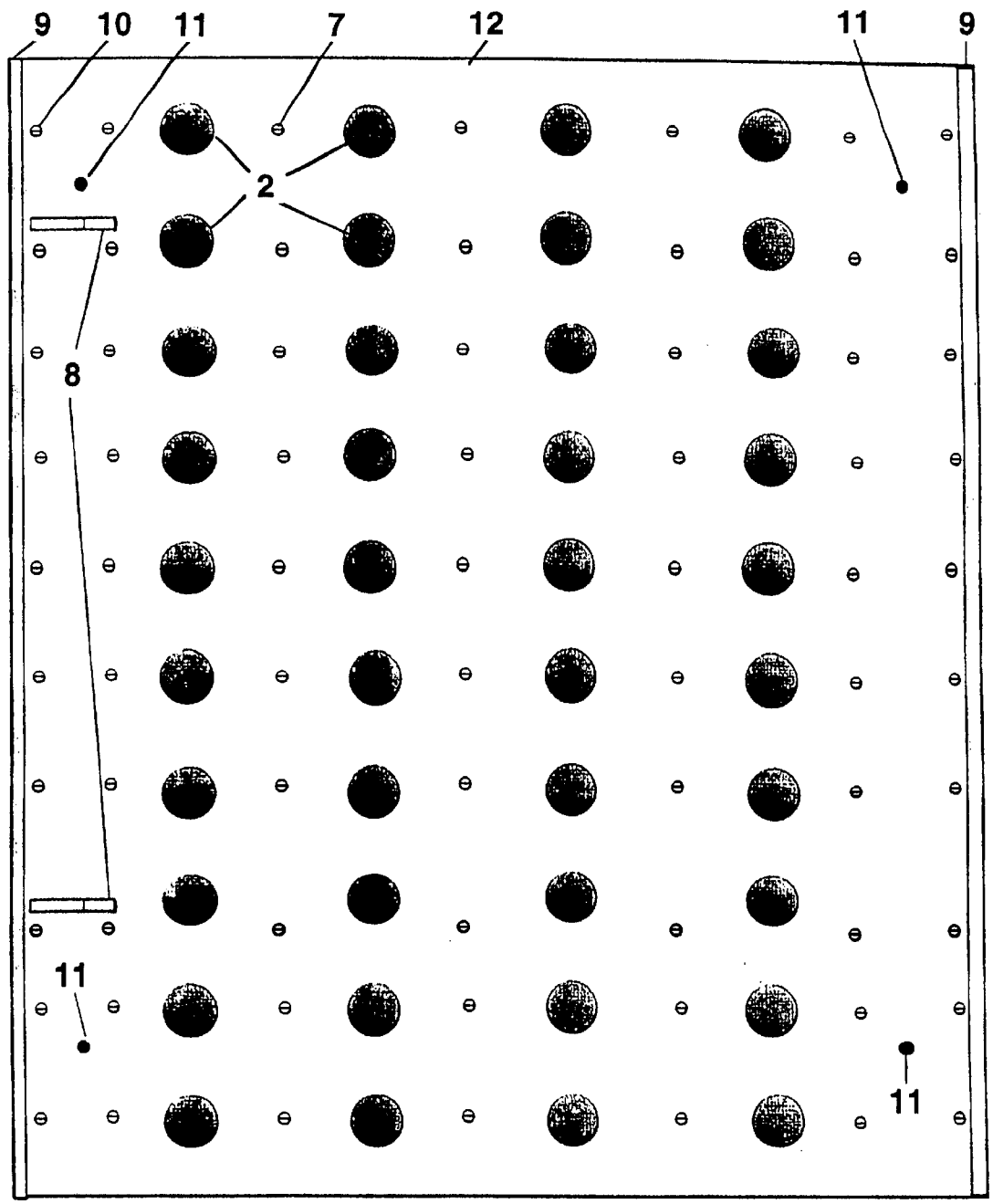
FIG. 9 is a plan view of the reaction plate of FIG. 7.

Referring now to FIG. 9, a schematic drawing showing the top view of the Teflon reaction plate 1. The top of the plate has a series of holes in a 4×10 matrix. Each hole has inserted a rubber gasket or disk 2. The outer edge of the Delrin bearing 9 can be seen. All of the Teflon plates are held together by a series of threaded screws 7. The gas inlet and outlet tubes 8 run perpendicular to the Delrin bearing 9.

Figure 10:
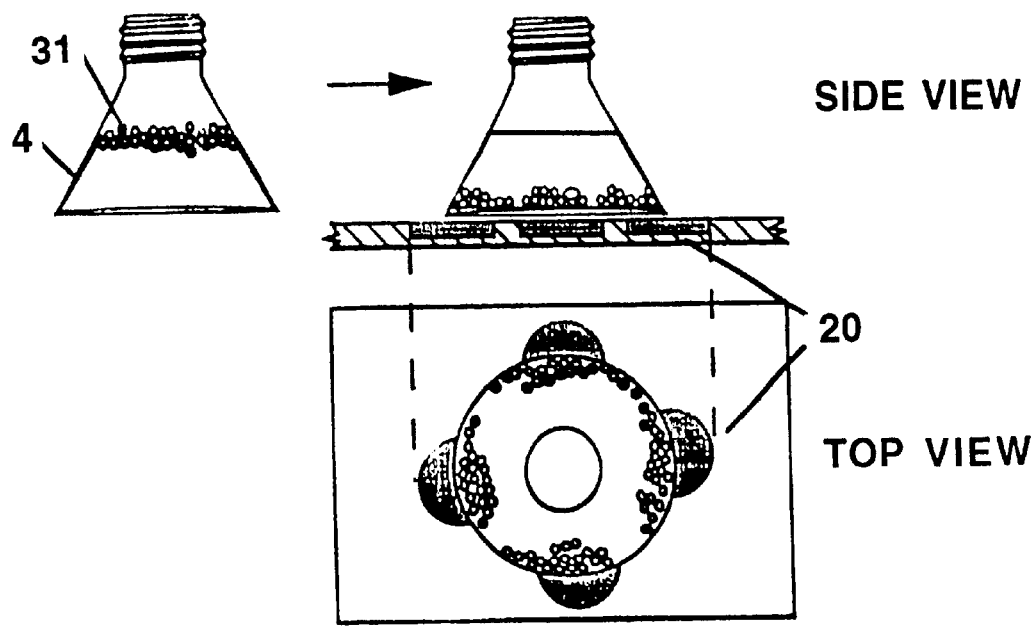
FIG. 10 is a schematic view of the position of the paramagnetic beads in the vessels of FIG. 7 during the steps of the magnetic separation process.

Referring now to FIG. 10, a schematic drawing showing the process of magnetic separation is provided. Paramagnetic particles 31 floating in methylene chloride (methylene chloride is denser than the particles) reaction flask 4 is shown. The neodymium magnetic discs 20 are arranged in such a manner that the magnetic field emanating from the discs results in accumulation of the paramagnetic beads at the bottom outer edges of the flask. The top view of the flask shows the particles congregating around the bottom edges where the magnetic discs are located, leaving the center free of particles. When a means for aspirating the solvent is present, activation of the means results in removal of the solvent; the paramagnetic beads are retained.

Figure 11:
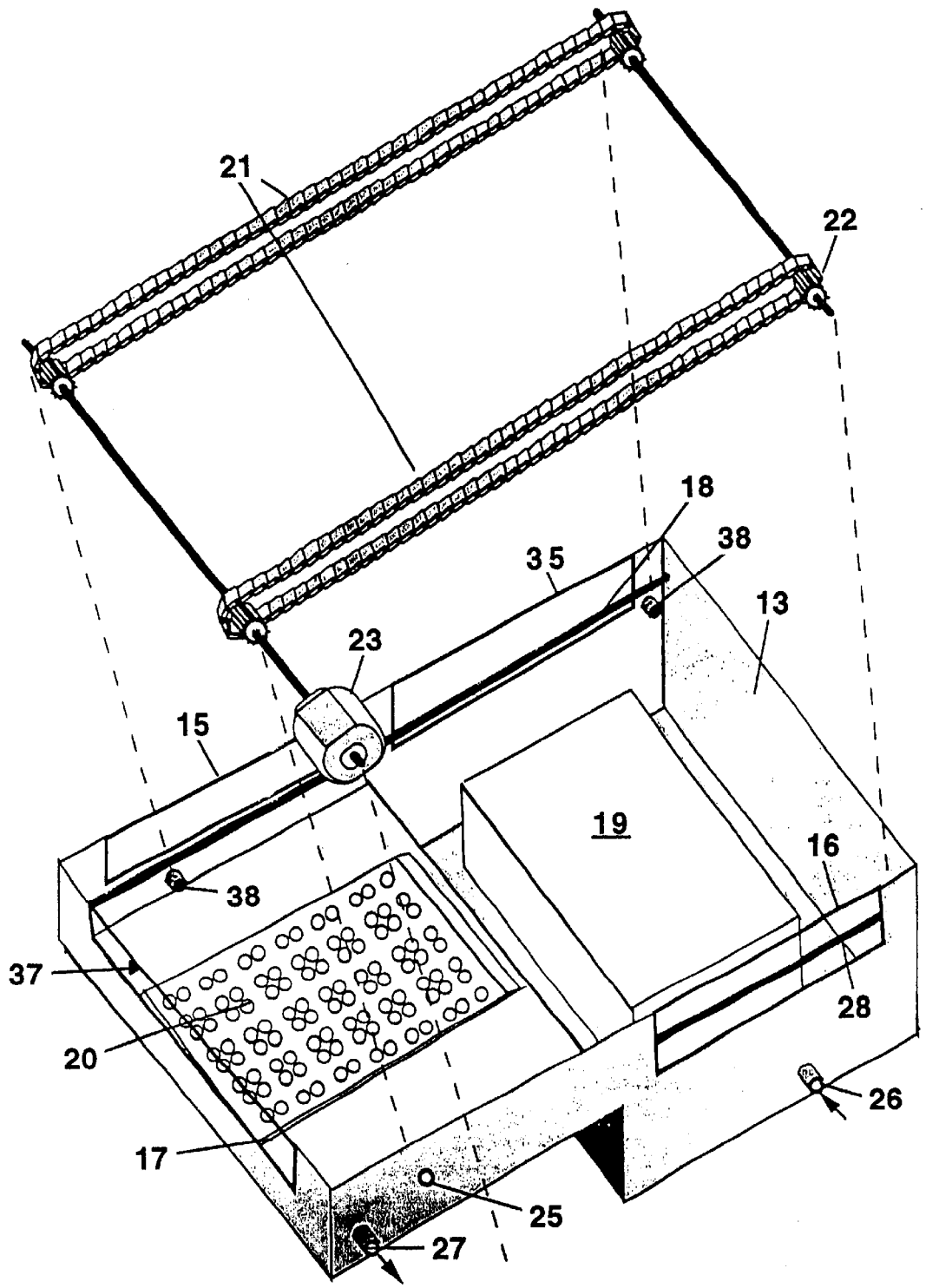
FIG. 11 is an isometric view of an alternative embodiment of the means for transporting the reaction plate of FIG. 7, the means for transporting being a partially exploded view to show the water bath in which is seated an ultrasonic field generating means and a magnetic force means.

Referring now to FIG. 11, a second embodiment of the means for transporting is illustrated. FIG. 11 shows a 3-dimensional exploded view of a belt drive 21 and motor assembly 23 which facilitates the movement of the reaction plate from region to region in the water bath. The water bath 13 is segregated into two differentiated regions: one wherein ultrasonic waves are emitted and one providing a magnetic field. The belt drive 21 is made of nylon and is turned by a computer controlled stepper motor 23 through the turning of a series of gears 22. The water bath 13 is made of aluminum and is divided into a sonication region and a magnetic separation region. The water bath has four windows 35, 15, 17, 16 each composed of acrylic sandwiched between two sheets of glass. Located in the sonicating region of the bath is a 25 kHz or 40 kHz frequency, immersible, variable amplitude immersible transducer 19 with an ultrasonic power of 600 Watts (obtained from Blackstone Ultrasonics, Jamestown, N.Y.). The sonicating transducer 19 is mounted to the bottom of the bath with all electrical wires leading out through a water-tight hole at the bottom of the bath located under the sonicator. The magnetic separation region 37 is composed of 160 nickel coated, neodymium magnetic disks (Master Magnetics, Castle Rock, Colo.) embedded in acrylic sheeting and topped with a thin sheet of Teflon. The entire composite is bolted to the bottom of the aluminum tank. On one side of the bath is inserted at opposite ends an inlet 26 and outlet port 27 to allow the free flow of water that has been chilled or heated using a commercially available temperature controlled (−20° C.–150° C.) water circulating bath (model 1140A, VWR Scientific, Plainfield, N.J.). The belt drive 21 and gears 22 are mounted to inner sides of the bath 38. The stepper motor is attached to the outside of the bath and is connected to the gears 22 through a hole 25 on the side of the bath. Two guide bearing rods 18, 28 made of stainless steel are bolted parallel and next to the nylon belts 21.

The means for transporting is not limited to the above two exemplified embodiments nor does the first or the second embodiment of the reaction plenum require the use of the particular means for transporting illustrated therewith. Alternative means such as gears, sprockets and a rod assembly or pulleys and cords or a rotating table or a 360 degree robotic hand such as available from Zymark, Hopkinton, Mass. could be used as long as the surface of the solvent in the vessel(s) being transported is substantially undisturbed and sloshing of the solvent is minimized especially when a small volume is present. Further, the motor which is part of the means for transporting is not unduly restricted, although computer-controllability is desired. A stepper motor is preferred when small volumes are used so that the starting and stopping of the reaction plate holding the vessels can be achieved relatively smoothly, again to preventing sloshing. Such stepper motors can be obtained, for example, from New England Affiliated technologies, Lawrence, Mass. and American Precision Industries, Woburn, Mass. Manual manipulation is also possible, however the efficiency of the machine is reduced.

The transporting can also be done by having the reaction plate stationary, and moving the magnetic field and the ultrasonic field into the region of the reaction plate so that they are effective upon the material in the flasks in the reaction plate. Movement of the fields can be accomplished by moving the means for creating the fields, or in some other manner such as by having both the magnetic field creating means and the ultrasonic field creating means positioned so that both fields are operative upon the material to be treated, and then selectively activating the fields as desired. This could be done, for example, if the magnetic field were created by electromagnetic means whereby electrical energy to the means could be provided when the field was to be activated, and then stopped when the field was no longer to be used.

Figure 12:
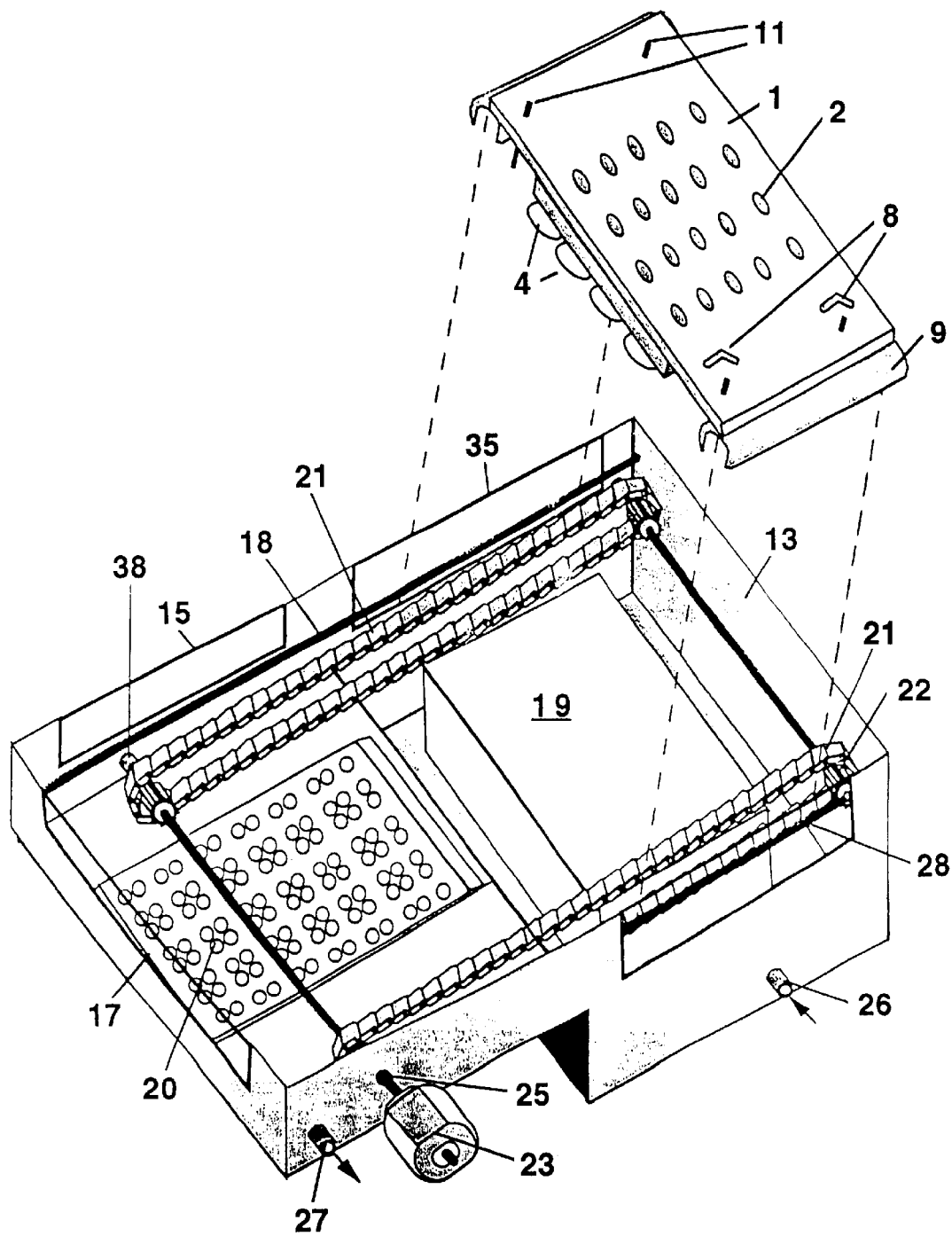
FIG. 12 is an isometric view of the positioning of the reaction plate relative to the means for transporting of FIG. 11.

Referring now to FIG. 12, an exploded view of the second embodiment of the reaction plenum with the positioning of the reaction plate 1 relative to the water bath 13 with the belt drive and motor assembly 21,22, 23 fully mounted on each of the inner sides of the bath 38 is provided. Two Delrin bearings 9 are attached to the reaction plate 1 on opposite sides of the plate 1. These bearings are aligned on top of the stainless steel rods 18, 28. A series of pins are passed through the holes of the plate 11 and on to the nylon belt 21. The motor 23 turns the gears 22 which turns the belts 21. As the belts 21 move they engage the reaction plate at the pins through the plate holes 11. The reaction plate is guided by the Delrin bearings 9 sliding along the stainless steel rods 18, 28. The reaction plenum is made such that a user may remove the belt drive 21 and manually move the reaction plate 1 along the two guide bearing rods 18, 28.

Figure 13B:
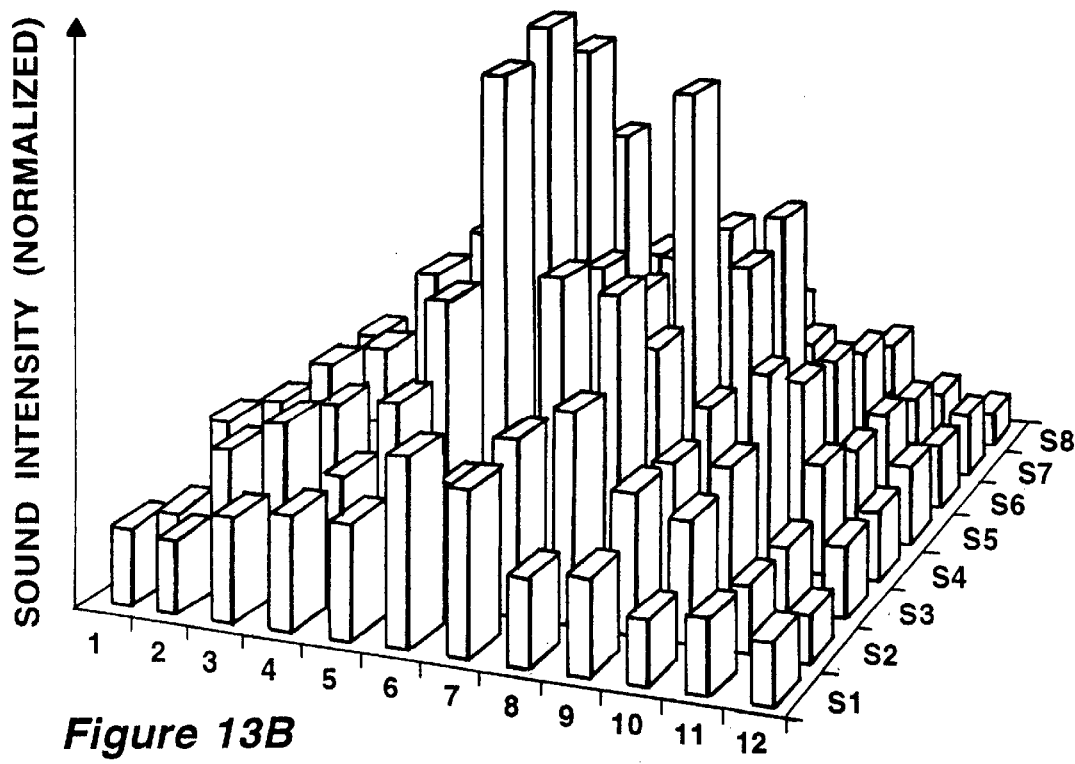
FIG. 13A is a schematic isometric view of a 20 kHz sonicating cup horn.
FIG. 13 B is a graph of the frequency intensity distribution of the sonicating cup horn of FIG. 13A.
Figure 13A:
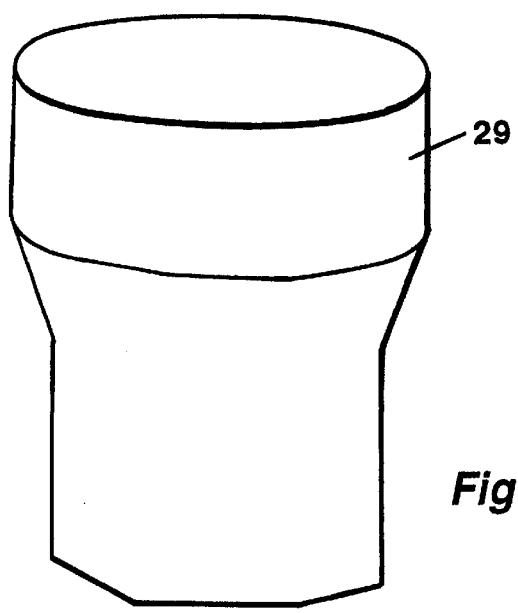

Referring now to FIGS. 13A and 13B, FIG. 13B provides a graphical representation of a Misonix's brand (Farmingdale, NY) 20 kHz sonicating cup horn 29 having a radiating face diameter of 2.25 inches and 550 watts power. FIG. 13B which is above the radiating face of the cup horn, a 3-dimensional bar graph representing the distribution of the sound intensity in an area of 3.25 inches×4 15/16 inches as measured using a commercially available immersible spot poled ceramic hydrophone (Specialty Engineering Associates, Soquel, Calif.) positioned 1.3 centimeters above the radiating face.

Figure 14B:
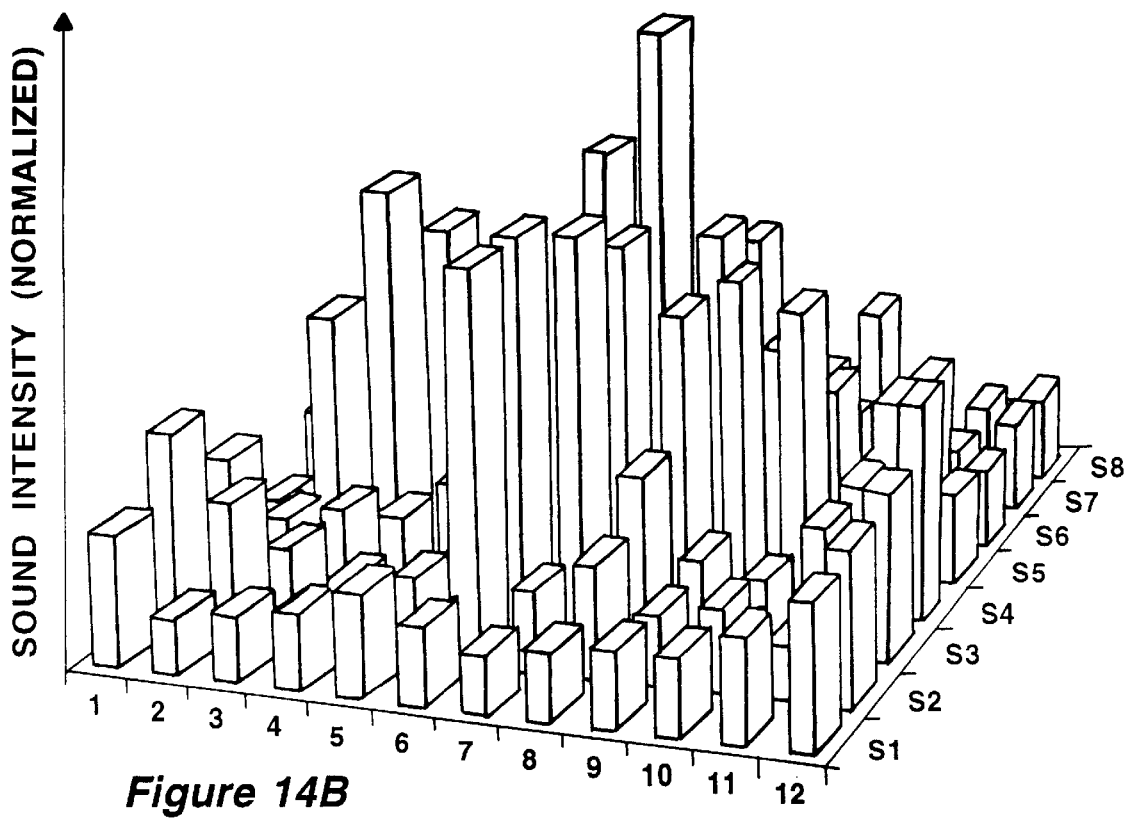
FIG. 14B is a graph of the frequency intensity distribution of the sonicating bar horn of FIG. 14A.
Figure 14A:
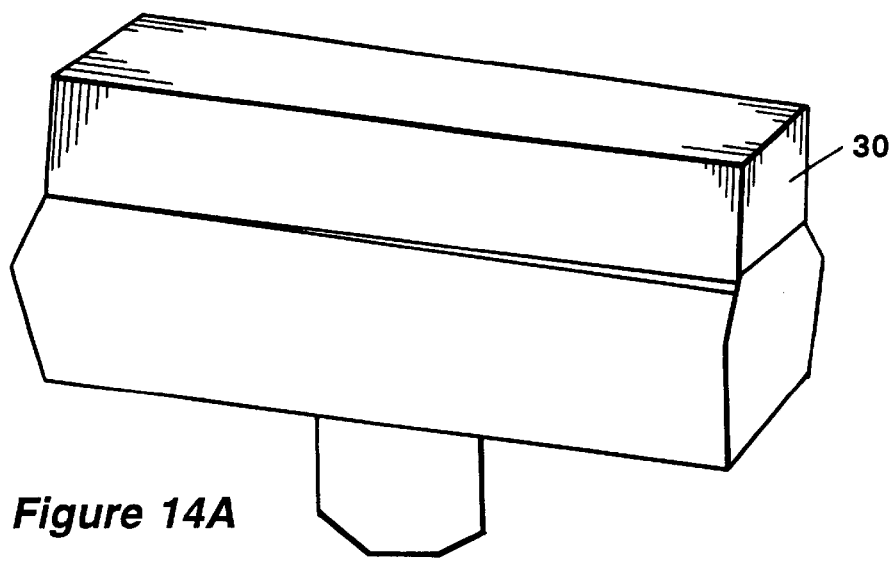
FIG. 14A is a schematic isometric view of a 30 kHz sonicating bar horn.

Referring now to FIGS. 14A and 14B, FIG. 14A schematic is a representation of a Misonix's brand (Farmingdale, N.Y.) 20 kHz sonicating bar horn 30 having a radiating face area of 5.6 inches×2 inches and 550 watts power. FIG. 14B shown above the radiating face of the sonicating bar horn, is 3-dimensional bar graph representing the sound intensity in an area in a water bath of 3.25 inches×4 15/16 inches as measured using a commercially available immersible spot poled ceramic hydrophone (Specialty Engineering Associates, Soquel, Calif.) positioned 1.3 centimeters above the radiating face.

Figure 15B:
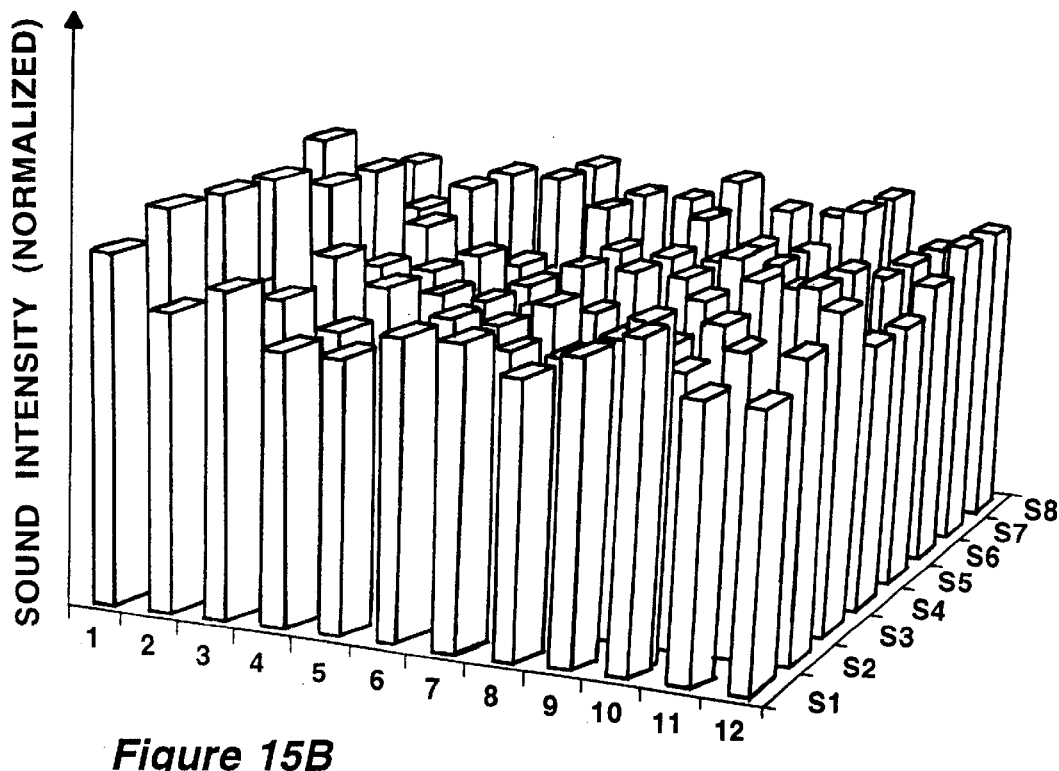
FIG. 15B is a graph of the frequency intensity distribution of the sonicating transducer of FIG. 15A.
Figure 15A:
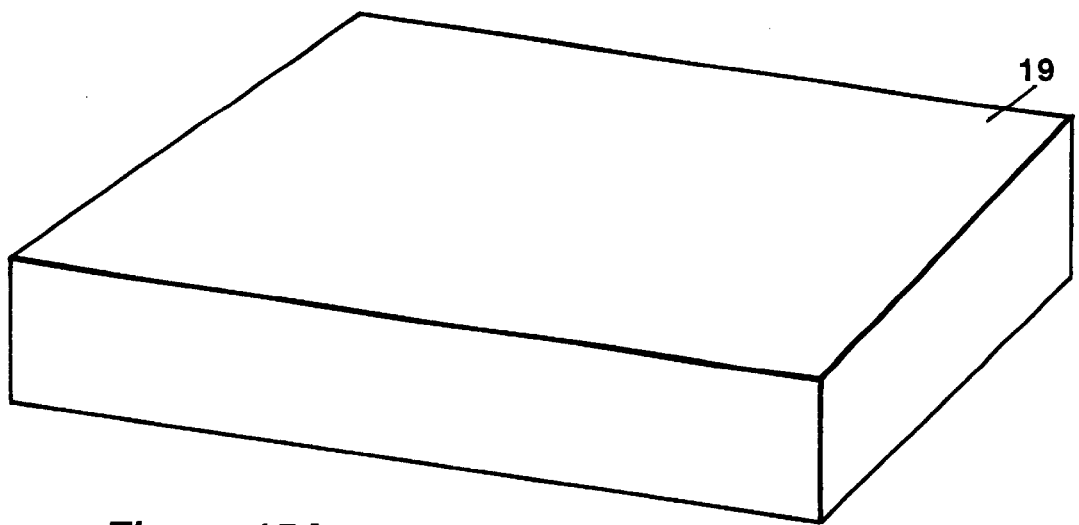
FIG. 15A is a schematic isometric view of a 25 kHz sonicating transducer.

Referring now to FIGS. 15A and 15B, FIG. 15A is a schematic representation of a Blackstone Ultrasonic's brand (Jamestown, N.Y.) immersible 25 kHz sonicating transducer (19) having a radiating face area of 6.7 inches×8.2 inches and having an ultrasonic power of 600 watts. FIG. 15A is shown above the radiating face of the immersible sonicator as a 3-dimensional bar graph representing the sound intensity in an area in a water bath of 3.25 inches×4 15/16 inches as measured using a commercially available immersible spot poled ceramic hydrophone (Specialty Engineering Associates, Soquel, Calif.) positioned 1.3 centimeters above the radiating face.

The variable amplitude, ultrasonic waves produced by the immersible sonicating transducer 19 travel through the water of the bath, through the glass Erlenmeyer flasks 4 and to the paramagnetic beads within 12 causing an enhancement of the reaction rate of a solid phase reaction and/or assisting in the mixing of the reaction mixture, depending upon the amplitude of the sound utilized. This occurs only when the reaction plate is positioned over the sonicating region of the bath. Upon activation of the motor 23, the reaction plate 1 moves longitudinally to the area of the bath containing the neodymium magnetic arrays 20. Once positioned over these arrays the magnetic particles 31 become attracted to the bottom of the flasks. This allows for the manual or automated removal of the solvent and the soluble components of the reaction mixture from the center of the flasks through suction. Upon reversing the rotation of the motor 23 the reaction plate can again longitudinally slide back over the sonication region of the water bath. The reaction plate may repeatedly slide back and forth between the sonication region and the magnetic separation region depending on the task to be performed. The reaction block may be used manually or can be automated. The preferred embodiment has the reaction block integrated with a commercially available x-y-z automated solvent delivery robot (the dispensing robot).

Figure 16:
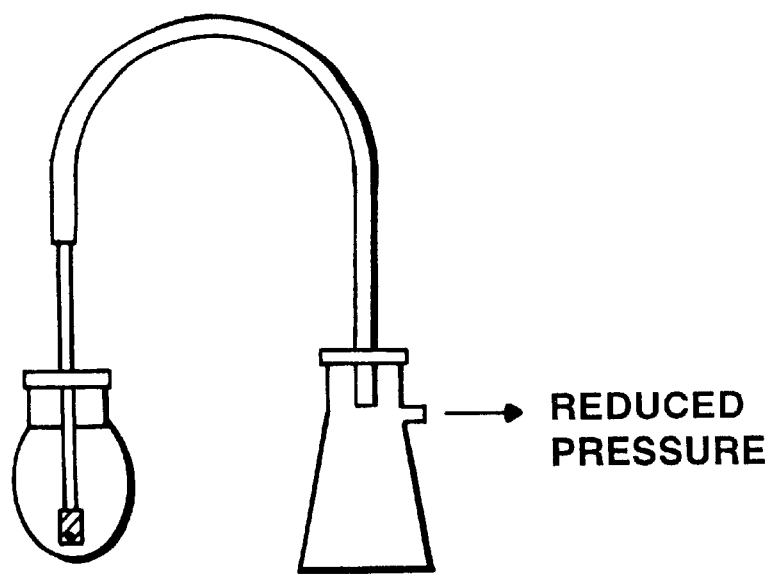
FIG. 16 is a schematic view of a reaction vessel incorporating a reverse filtration manifold.

The use of reverse filtration with non-paramagnetic beads is described in detail in Example 10 when taken in conjunction with the schematic illustration of FIG. 16. The specific components of FIG. 16 are also described in detail within the description of Example 10.

Figure 17:
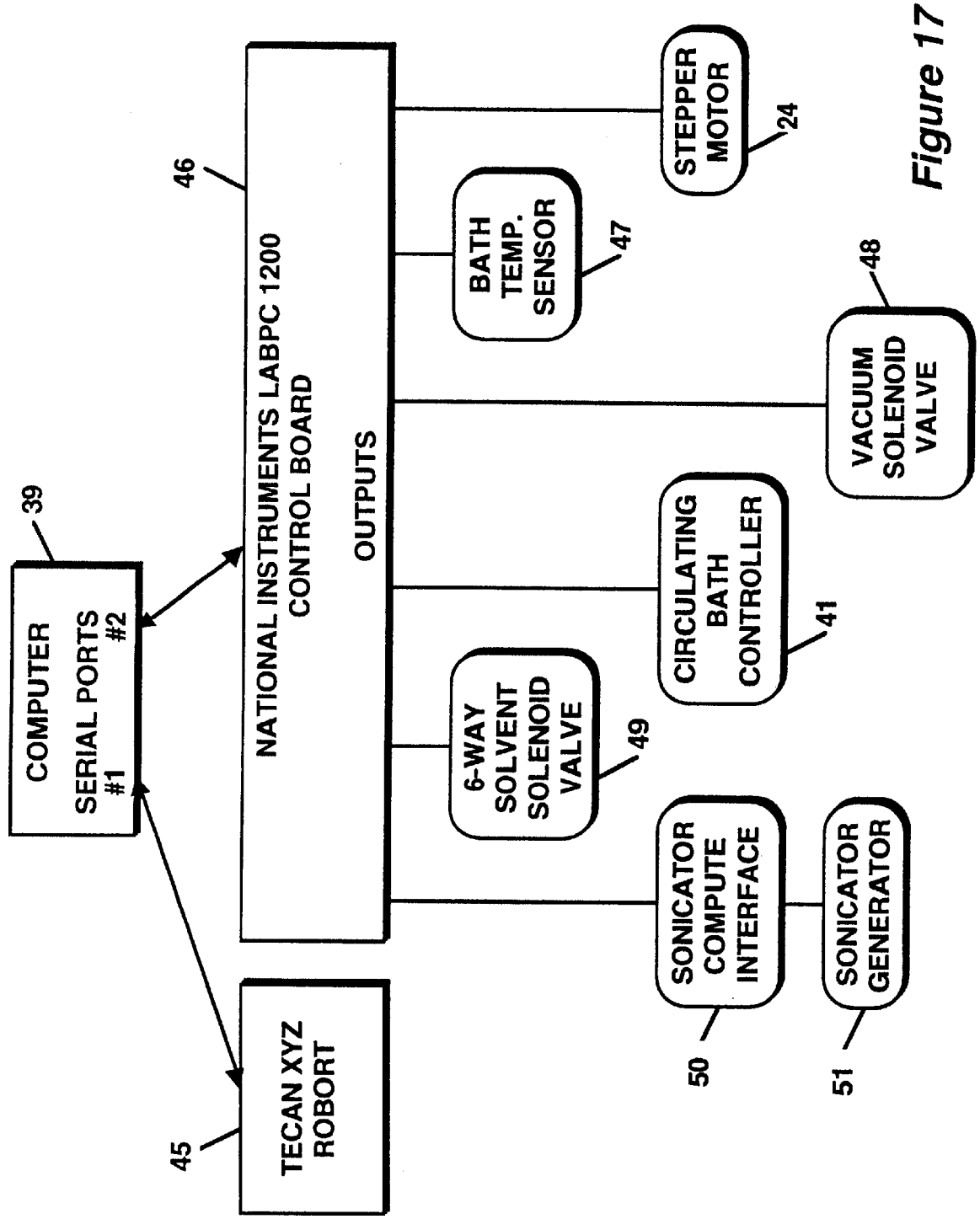
FIG. 17 is a schematic diagram of the electrical system for the entire automated reaction plenum.

Referring now to FIG. 17, is a schematic representation of the electrical system of the automated reaction plenum. A computer 39 is connected through port #1 to a liquid handling robot 45. From a second port #2 on the computer, a control board 46, such as a National Instruments brand LabPC control board, is connected. From this control board a series of input/output devices are connected which include the stepper motor 24, a sonicating bath temperature sensor and on/off controller 47, a vacuum solenoid valve 48 which controls aspiration, a circulating bath controller 41, a 6-way solenoid valve 49 which controls up to 6 different solvents for liquid addition, and the immersible sonicator system which includes a sonicator computer interface 50 and a sonicator generator 51. A user can activate any or all of the devices in whatever order the user requires, and can be accomplished, for example, using a computer script language.

Thus, the computer control system shown in FIG. 17 is designed to provide integrated control of laboratory functions (sonication, magnetic separation, aspiration, etc.) to create a unified system for running organic chemical reactions. The main instrumentation components of the system include the stepper motor 24 which controls mobile reaction plate 1, the variable amplitude sonicator 51, the liquid handling robot 45, the series of solenoid valves 49 and the temperature controlled water circulating bath 41. The control system includes the control system software and a National Instruments LabPC1200+ Multi-purpose Data Acquisition Board. The control system software and hardware combine to unify the instrumentation components into a flexible system allowing the user to run the various operations under full automation or under manual control.

The control system is composed of two components, the Data Acquisition hardware and the control software. The control software is designed to provide the user with the ability to create customized tests using the instrumentation system. The system provides a simple programming language containing commands to control various aspects of the control system. These commands can be used in any combination to create custom test sequences.

When the control program runs, it initializes the control circuitry. There is a status window on the main screen of the display (such as a CRT, for example) which provides a notice declaring that the hardware is being initialized. This process lasts a few seconds, and, when it is complete, the status window will display a message indicating that it is safe to proceed to other program functions. There is an emergency stop provided by the computer and which can be actuated by the user.

The control system also provides a means of directly controlling the instrumentation hardware in a manual mode. This feature, known as manual control, is accessed from the computer program menu. The user can use the various controls on this window to control the various components of the instrumentation system. The sonicator can be manually controlled by the computer. To adjust the power level of the sonication, the user moves a slider control to the appropriate percentage (0 to 100) and initiates the sonicating process. To stop the sonication, the user presses the appropriate computer control to turn the sonicator off.

The reaction plate can be manually moved back and forth using another set of computer controls. First, the user selects a motor speed by moving the control appropriately. This control specifies a speed as a percentage of the maximum speed.

The vacuum solenoid valve 48 controlling the aspirator functions can be actuated by the computer program, either automatically or manually, depending upon which type of operation is being used. This can be used to toggle the solenoid on and off. The 6-way solenoid valve 49 is operated in the same manner with the user controlling the "6-way solenoid" from the computer. The program can then be instructed as to which of the six valves are to be opened. The user then designates the specific valve to be opened.

In order to further specify the process of this invention, the following examples are provided. It will be recognized by those skilled in the art that these examples represent only specific implementations of the apparatus and method of use of the invention. They are not intended to limit its scope.

EXAMPLE 1

Stepwise Synthesis of Glycyl-Alanyl Linker on Magnetic Composite Particles (Scheme 1).

a) Coupling and Deprotection of Linker (3). To one of the reaction vessels mounted in the reaction vessel plate seated in the reaction plate holder is added 25 mg (0.017 mmole) paramagnetic composite polystyrene beads having aminomethyl groups coupled thereto 1 (obtained from Polymer Laboratories, Church Stretton, UK, which are the ones disclosed in pending application Ser. No. 08/585,905, filed Jan. 16, 1996). Using a commercially available X-Y-Z Tecan Liquid Handling Robot (Research Triangle Park, N.C.) a solution of 50 microliters (11.4 mmole) of diisopropylethylamine dissolved in 1.5 mL of methylene chloride is added by robotic needle syringe. The water bath temperature is set at 25° C. using a commercially controlled (−20° C. to 150° C.) water circulating bath (model 1140A, VWR Scientific, Plainfield, N.J.) which is connected to the entrance and exit ports of the bath. The mixture is then sonicated using the Misonix's brand (Farmingdale, N.Y.) immersible sonicator (25 kHz or 40 kHz) with a power of 600 watts for 1 minute. After 1 minute the reaction vessel is moved to the magnetic separation region and after another 1 minute interval, the liquid in the reaction vessel is aspirated using the Tecan liquid handling robot. To the reaction vessel is then added 2–3 ml of methylene chloride. The mixture is then sonicated on low power for 30 seconds. The reaction vessel is then moved to the magnetic separation region and the solvent removed by aspiration. This process is repeated two more times. Using the Tecan liquid handling robot for dispensing, first 42.5 mg (0.078 mmole) of p-[(R,S)-a-[1-9H-fluoren-9-yl)-methoxbenzyl]-phenoxyacetic acid (Fmoc) linker 2 (Scheme 1) dissolved in 1.5 mL of dimethylformamide and then 12.5 microliters (0.079 mmole) of diisopropylcarbodiimide (DIC) dissolved in 1.5 mL of anhydrous methylene chloride in that order is added to the reaction vessel.

Scheme 1

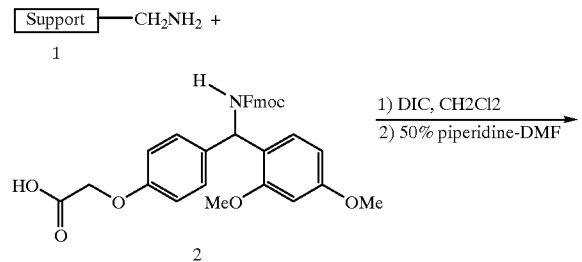

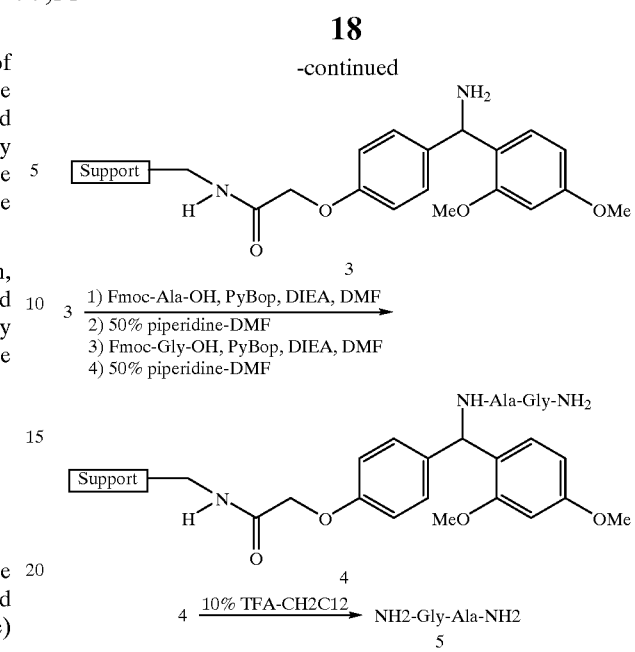

The water bath temperature is set at 25° C. using a commercially available temperature controlled (−20° C. to 150° C.) water circulating bath (model 1140A, VWR Scientific, Plainfield, N.J.) which is connected at the entrance 26 and exit 27 ports (FIG. 5) of the reaction plenum. The mixture is then sonicated on low energy for a period of 6 hours. Next, the reaction vessel is longitudinally transported to the magnetic separation region where the soluble components of the reaction mixture are removed by aspiration using the Tecan robot. The paramagnetic beads are washed by adding 2–3 ml of methylene chloride, sonicating the mixture at low power for 30 seconds, immobilizing the paramagnetic beads in the magnetic separation region and aspirating the solvent. Washing is repeated three more times. Next, 50 microliters (0.285 mmole) of DIEA dissolved in 1 mL of methylene chloride and 25 microliters (0.26 mmole) of acetic anhydride dissolved in 0.5 ml of methylene chloride are added to the reaction vessel. The mixture is sonicated on low power for a period of 1 hour. The reaction vessel is then transferred to the magnetic separation region and the soluble components of the reaction mixture removed by aspiration using the liquid robotic arm. To the reaction vessel is added 2 ml of methylene chloride which is then sonicated on low power for 20 seconds. The reaction vessel is moved to the magnetic separation region and the solvent removed by aspiration. This washing process is then repeated two more times. The washing process is then performed with 2 ml of methanol a total of two times and then finally a wash with methylene chloride a total of three times is performed, in that order.

b)Synthesis of Gly-Ala bound to Rink amide linker 3 (Scheme 1). In this Example, a-N-Fmoc-substituted amino acids are abbreviated Fmoc-Xxx, where Xxx is the conventional three-letter abbreviation for any of the amino acids. To the Fmoc protected paramagnetic particles of the previous example is added 0.4 mL of 50% piperidine in dimethylformamide and the mixture is sonicated on low power for a period of 20 minutes. The water bath temperature is set at 250° C. using a commercially available temperature controlled (−20 C. to 150° C.) water circulating bath (such as model 1140A, VWR Scientific, Plainfield, N.J.) which is connected at he entrance 26 and exit 27 ports (FIG. 11). The reaction vessel is then transferred to the magnetic separation region and the soluble components of the reaction mixture removed by aspiration using the Tecan robot. Dimethylformamide (DMF) wash procedure: To the reaction vessel is then added 3 ml of dimethylformamide and the contents are sonicated on low power for 30 seconds. The reaction vessel is then moved to the magnetic separation region and the solvent is removed by aspiration. The DMF wash is repeated three more times. Then a wash with 2 ml of methanol using the DMF wash protocol a total of two times is performed. Finally, a wash with methylene chloride a total of three times is performed. To the deprotected particles 3 (Scheme 1) is added a solution of 32 mg (0.1 mmoles) of a-N-Fmoc-Ala in 0.5 mL of DMF, 50 mg (0.1 mmole) of benzotriazole-1-yl-oxy-tris-pyrrolidino-phosphonium-hexafluorophosphate (PyBop) in 0.5 mL of DMF and 40 microliters (0.23 mmole) of diisopropylethylamine in 1 mL of DMF and the mixture is sonicated on low power for a period of 2 hours. The reaction vessel is then transferred to the magnetic separation region and the soluble components of the reaction mixture removed by aspiration using the Tecan robot. A DMF wash as described above is repeated four times. Then using the DMF protocol, the paramagnetic beads are washed twice with 2 ml of methanol and then three times with 2 ml methylene chloride, in that order. To the reaction vessel is then added 0.4 mL of 50% piperidine in dimethylformamide and the mixture is sonicated on low power for a period of 20 minutes. The reaction vessel is then transferred to the magnetic separation region and the soluble components of the reaction mixture removed by aspiration using the Tecan robot. A DMF wash is performed four times as described above. Then using the DMF wash protocol with 2 ml of methanol, a wash is performed twice. Finally, the paramagnetic beads are washed with methylene chloride a total of three times. Coupling and deprotection of Fmoc-Gly is accomplished in the same manner as just described for the first Fmoc-Ala reaction. After piperidine deprotection, covalently bound Gly-Ala-linker-resin paramagnetic composite particles 4 (Scheme 1) are provided.

EXAMPLE 2

Cleavage of Gly-Ala Off Magnetic Composite Particles (Scheme 1)

To dried resin 4 (Scheme 1) is added 3 mL of a 10% trifluoroacetic acid (TFA) in methylene chloride and the mixture is sonicated on low power for 20 minutes. The particles are magnetically separated and the liquid is siphoned off using the Tecan robot. To the particles is added another 3 mL of 10% TFA-CH$_2$Cl$_2$ solution and the mixture is sonicated on low power for a total of 20 minutes. The particles are again magnetically separated. The liquid is aspirated off and combined with the previous acid wash, and the volatile components are removed under reduced pressure to give an oil. The oil is precipitated from diethyl ether to give the dipeptide 5 (Scheme 1) as the trifluoroacetic acid salt.

Scheme 2

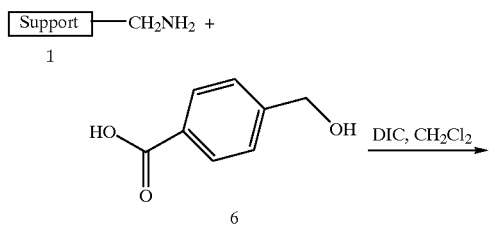

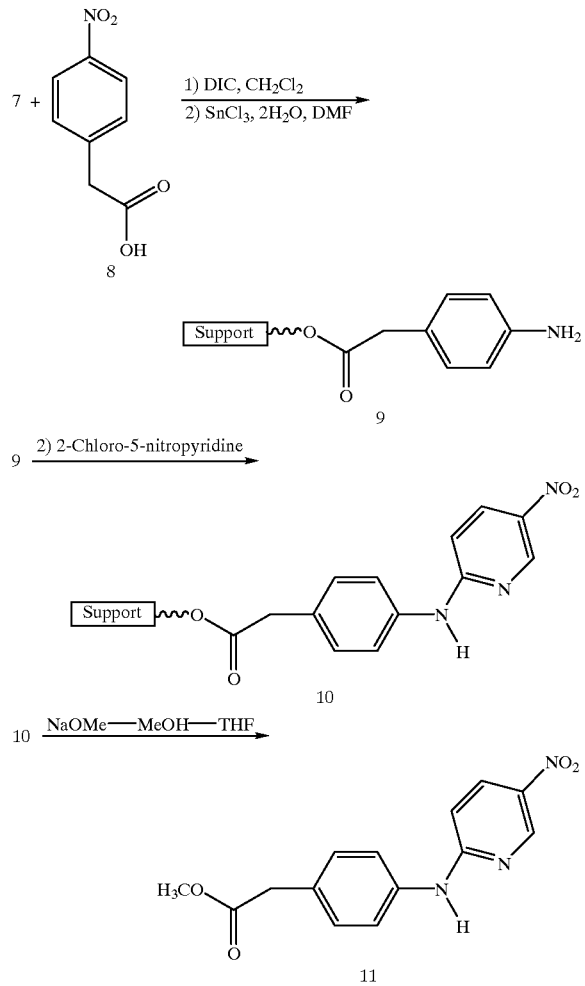

EXAMPLE 3

Automated Stepwise Synthesis of Resin Bound 4-Aminophenyl Acetate (9) (Scheme 2)

a) Coupling of Linker (6). To one of the flasks mounted in the reaction plate is added 25 mg (0.017 mmole) of aminomethyl magnetic composite particles 1 (obtained from Polymer Laboratories, Church Stretton, UK, which are the ones disclosed in pending application Ser. No. 08/585,905, filed Jan. 16, 1996). Using a commercially available one arm x-y-z Tecan 505 liquid handling robot (Research Triangle Park, N.C.) a solution of 50 microliters (11.4 mmole) of DIEA dissolved in 1.5 mL of methylene chloride is added by needle syringe. The water bath temperature is set at 25° C. using a commercially available temperature controlled (−20°C. to 150° C.) water circulating bath (model 1140A, VWR Scientific, Plainfield, N.J.) which is connected at the entrance 26 and exit 27 ports of the reaction plenum (FIG. 5). The mixture is then sonicated using the Blackstone Ultrasonics brand immersible sonicator (25 kHz or 40 kHz) (19, FIG. 5) for 1 min. After 1 min. the Erlenmeyer flask is transferred to the magnetic separation region and after 1 minute, the liquid in the flask is aspirated using the Tecan liquid handling robot. To the flask is then added 2–3 ml of methylene chloride and sonicated on low power for 30 seconds. The Erlenmeyer flask is then moved to the magnetic separation region and the solvent removed by aspiration. This process is then repeated two more times. To the flask containing 1 (Scheme 2) is then added using the Tecan liquid handling robot 12 mg (0.078 mmole) of linker 6 (Scheme 1) dissolved in 1.5 mL of dimethylformamide and then 12.5 microliters (0.079 mmole) of DIC dissolved in 1.5 mL of anhydrous methylene chloride in that order. The mixture is then sonicated on low energy for a period of 5 hours. The flask is then transferred to the magnetic separation region and the soluble components of the reaction mixture removed by aspiration using the Tecan robot. To the flask is then added 2–3 ml of methylene chloride and sonicated on low power for 30 seconds. The flask is then moved to the magnetic separation region and the solvent removed by aspiration. This process is then repeated three more times to give resin bound 7 (Scheme 2).

b)Synthesis of resin bound 9. To the flask containing 7 (Scheme 2) is then added using the Tecan liquid handling robot 14 mg (0.078 mmole) of 4-nitrophenylacetic acid (8, Scheme 2) dissolved in 1.5 mL of dimethylformamide and then 12.5 microliters (0.079 mmole) of DIC dissolved in 1.5 mL of anhydrous methylene chloride in that order. The water bath temperature is set at 25° C. using a commercially available temperature controlled (−20° C. to 1500° C.) water circulating bath (model 1140A, VWR Scientific, Plainfield, N.J.) which is connected at the entrance 26 and exit 27 ports (FIG. 5). The mixture is then sonicated on low energy for a period of 5 hours. The flask is then transferred to the magnetic separation region and the soluble components of the reaction mixture removed by aspiration using the Tecan robot. To the flask is then added 2–3 ml of methylene chloride and sonicated on low power for 30 seconds. The flask is then moved to the magnetic separation region and the solvent removed by aspiration. This process is then repeated three more times each with dimethylformamide, methanol and methylene chloride in that order. To the flask is then added 200 mg (0.88 mmole) of $SnCl_2.2H_2O$ dissolved in 1.5 ml of dimethylformamide and flask sonicated on low power for 6 hours. The flask is then transferred to the magnetic separation region and the soluble components of the reaction mixture removed by aspiration using the Tecan robot. To the flask is then added 2–3 ml of dimethylformamide and this is sonicated on low power for 30 seconds. The flask is then moved to the magnetic separation region and the solvent removed by aspiration. This process is then repeated three more times with dimethylformamide and then three times with methanol and then three times with methylene chloride in that order. To the resin is then added 4 ml of dimethylformamide and mixture is sonicated under low power for 5 hours. The flask is moved to the magnetic separation region and the solvent is removed by aspiration. To the flask is then added 2–3 ml of methanol and this is sonicated on low power for 30 seconds. The flask is then moved to the magnetic separation region and the solvent is removed by aspiration. This process is then repeated two more times with methanol to give resin bound aminophenyl acetate (9, Scheme 2).

EXAMPLE 4

Comparison of Resin Washing With and Without the use of Sonication

This example is presented to demonstrate the effectiveness of sonication for resin washing of impurities in contrast to standard filtration washing. Resin bound aminophenyl acetate (9, Scheme 2) was synthesized as in Example 3 except that the unreacted $SnCl\phi 2H_2O$ was washed using standard filtration washing following the protocol: 5×DMF, 4×MeOH, 3×$CH_2Cl_2$ and 3×MeOH in that order to give Sample 9-A. Each wash involved shaking the resin mixture for 30 seconds before filtering. The level of tin in Sample 9-A was then measured using elemental analysis to be 1.71%. A portion of Sample 9-A was then stirred for 24 hours in dimethylformamide and then filtered and washed with methanol to give Sample 9-B. The level of tin in Sample 9-B was then measured using elemental analysis to be 0.36%. Another portion of Sample 9-A was sonicated (25 kHz or 40 kHz) on low power for 5 hours in dimethylformamide and then filtered and washed with methanol to give Sample 9-C. The level of tin in Sample 9-C was then measured using elemental analysis to be 0.33%.

EXAMPLE 5

Automated Synthesis of the Non-Peptide Compound 2-N-(p-aminophenylacetate)-5-nitropyridine (10) Using Magnetic Composite Particles With and Without the Use of High Energy Ultrasound (Scheme 2)

First, the water bath temperature is set at 25° C. using a commercially available temperature controlled (−20° C. to 150° C.) water circulating bath (model 1140A, VWR Scientific, Plainfield, N.J.) which is connected at the entrance 26 and exit 27 ports (FIG. 5). To one flask containing 25 mg of resin bound aminophenyl acetate (9, Scheme 2) is added 27 mg (0.17 mmoles) of 2-chloro-5-nitropyridine dissolved in 1.5 mL of dimethylformamide and mixture is sonicated at medium power and at room temperature for 7 hours. The flask is then transferred to the magnetic separation region and the soluble components of the reaction mixture removed by aspiration using the Tecan robot. To the flask is then added 2–3 ml of dimethylformamide and the flask is sonicated on low power for 30 seconds. The flask is then moved to the magnetic separation region and the solvent removed by aspiration. This process is then repeated three more times with dimethylformamide and then three times with methanol and then three times with methylene chloride in that order to give resin bound 10 (Scheme 2). To air dried resin 10 (Scheme 2) was added 1 mL of a 0.1 N solution of sodium methoxide in 50% methanol-tetrahydrofuran and mixture is sonicated on low power for 5 hours. The particles were magnetically separated and the liquid and the volatile components of the reaction mixture removed under reduced pressure to give 11 (Scheme 2) as the free base. Crude sample 11 (Scheme 2) was separated by reversed phased high pressure liquid chromatography coupled with positive ion electrospray mass spectrometry (HPLC-EIMS) to give two main UV active fractions. The largest UV active fraction which composed the majority (>90%) of the sample was identified as the desired product 11 (M+H=288) and the much smaller UV active fraction which composed less than 10% was identified as 4-aminophenylacetate (M+H=166).

To another flask containing 25 mg of resin bound aminophenyl acetate (9, Scheme 2) is added 27 mg (0.17 mmoles) of 2-chloro-5-nitropyridine dissolved in 1.5 mL of dimethylformamide and mixture stirred at room temperature for 7 hours. The flask is then transferred to the magnetic separation region and the soluble components of the reaction mixture removed by aspiration using the Tecan robot. The flask is then washed in the same manner as the previous reaction. To the dry resin was then added 1 mL of a 0.1 N solution of sodium methoxide in 50% methanol-tetrahydrofuran and mixture sonicated on low power for 5 hours. The particles were magnetically separated and the liquid and the volatile components of the reaction mixture removed under reduced pressure to give a residue which was purified and identified by reversed phased high pressure liquid chromatography coupled with positive ion electrospray mass spectrometry (HPLC-EIMS) as being mostly (>90%) 4-aminophenylacetate (M+H=166).

EXAMPLE 6

Manual Solid Phase Synthesis of Resin Bound 2-N-(p-aminophenylacetate)-5-benzamidepyridine (15) Using Modified Reaction Plenum (Scheme 3)

This example is used to demonstrate the use of the reaction plenum in a manual mode without the use of the Tecan liquid handling robot and the computer controlled, motorized plate mover. This entails the removal of the belt drive 21, gears 22 and motor assembly 23 from the reaction plenum (FIG. 5). The water bath temperature is set at 25° C. using a commercially available temperature controlled (−20° C. to 150° C.) water circulating bath (model 1140A, VWR Scientific, Plainfield, N.J.) which is connected at the entrance 26 and exit 27 ports (FIG. 5).

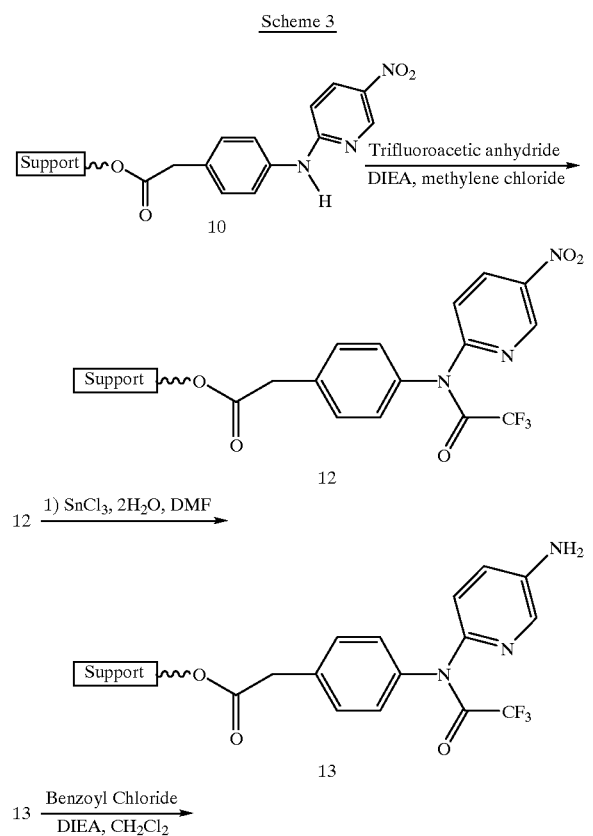

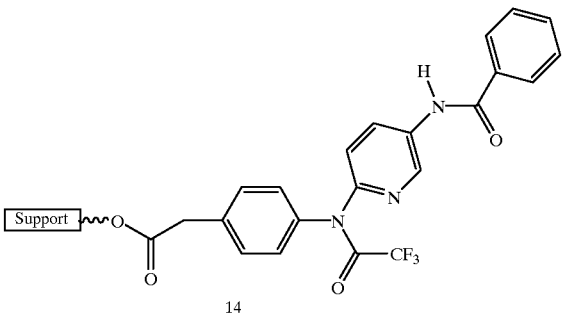

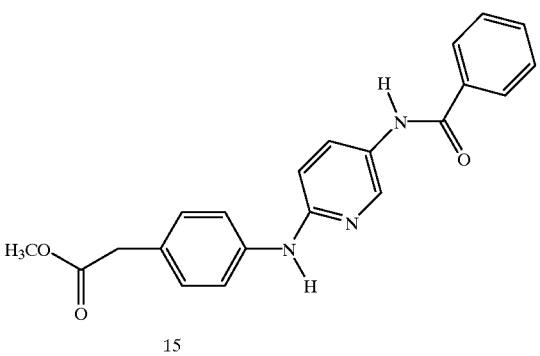

Use of the reaction plenum in manual mode entails the manual movement of the reaction plate from the sonication region (19, FIG. 5) to the magnetic separation region (20, FIG. 5). It also entails the manual addition of the reagents and the manual aspiration of the solvent using an aspiration tube or rake (for multiple reactions) connected to a vacuum trap.

To one of the 5 ml glass conical flasks (4, FIG. 1) attached to the reaction plate (1, FIG. 1) is added 100 mg of dry paramagnetic support (10, Scheme 3). To the flask is then manually added 2 mL of methylene chloride, 0.5 mL of diisopropylethylamine (DIEA) and 0.2 mL of trifluoroacetic anhydride. The mixture is allowed to sit under nitrogen atmosphere for 10 minutes. The reaction plate (1, FIG. 1) is then manually slid to the sonication region of the reaction plenum and mixture sonicated under low energy, under nitrogen atmosphere for 5 hours. The reaction plate (1, FIG. 1) is then slid to the magnetic separation region and mixture manually aspirated. To the flask is then manually added 3–4 ml of dimethylformamide and reaction plate is slid to the sonication region and mixture is sonicated for 15 seconds. The reaction plate is then slid to the magnetic separation region and the solvent manually aspirated. This procedure is repeated three more times with dimethylformamide, twice with methanol, once with methylene chloride and once with methanol and then dried under nitrogen atmosphere to give resin bound 12 (Scheme 3). To the conical flask containing 12 (Scheme 3) is added 3 mL of a 0.4 M $SnCl_2 \cdot 2H_2O$ in dimethylformamide. The reaction plate is then sonicated under low power for 5 hours. The reaction plate is then slid to the magnetic separation region and solvent aspirated. The resin is washed in the same manner as previous to give resin bound 13 (Scheme 3). To the dry resin bound 13 (Scheme 3) is then added 3 mL methylene chloride, 0.25 mL (1.43 mmoles) diisopropylethylamine (DIEA) and 0.15 mL benzoyl chloride (1.29 mmoles) and mixture is sonicated under low power and under nitrogen atmosphere for 5 hours. The resin is washed in the same manner as previous to give resin bound 14 (Scheme 3). To the conical flask is then added 3 mL of 0.2M sodium methoxide in 30% methanol-tetrahydrofuran (THF) and mixture is sonicated under low power for 5 hours. The reaction plate is then slid to the magnetic separation region and the soluble components of the reaction mixture are removed and evaporated to give crude 2-N-(p-aminophenylacetate)-5-benzamidepyridine (15, Scheme 3) as the methyl ester.

EXAMPLE 7

Comparison of the Uniformity of the Sonicating Field Produced by Three Transducer Sources Using an Immersible Hydrophone The following example compares the uniformity of the ultrasonic field produced by three different sonicating transducer sources and demonstrates the greater uniformity of the ultrasonic field produced by immersible transducer 19 (FIG. 5). A 96-well polypropylene plate (3.25 inches×15 inches×½ inch) embedded with 96 glass test tubes was positioned 1.3 centimeters above the radiating face of a Misonix's brand 20 kHz sonicating cup horn (29, FIG. 7) which was immersed under water. Each of the 96 test tubes was filled with diionized water and then the sonicating horn turned on at 30% power level. While the sonicator was activated, a spot poled ceramic hydrophone (Specialty Engineering Associates, Soquel, Calif.) which was connected to a Tektronix's brand (Beaverton, Oreg.) Oscilloscope was inserted into each of the water filled test tubes and the amplitude recorded. The amplitude of the sonicating wave was then plotted against each test tube position and a 3-dimensional bar graph was then constructed (FIG. 7).

The previous procedure was repeated using a Misonix's brand 20 kHz sonicating bar horn (FIG. 8). The amplitude of the measured sonicating wave was then plotted against each test tube position to give a 3-dimensional bar graph (FIG. 8). The process was again repeated with one of the Blackstone Ultrasonics brand immersible (20 kHz) sonicating transducers (19, FIG. 9) and a 3-dimensional bar graph was then constructed showing the sonicating intensity level at each test tube position (FIG. 9). This experiment was also done with the 40 kHz immersible sonicating transducer (Blackstone Ultrasonics) with identical results as that of the 20 kHz immersible transducer (19, FIG. 9). Comparison of the central region of each of the bar graphs shows the cup horn (29, FIG. 7) and the bar horn (30, FIG. 8), both probe type ultrasonic transducers exhibiting average maximum intensity variations of 60%. The immersible, bath type ultrasonic transducer (19) exhibited an average maximum intensity variation of 30%.

EXAMPLE 8

Automated Synthesis of the Non-Peptide Compound 9-N-(p-aminophentylacetate)acridine (18) in Solution (Scheme 4)

This example is used to demonstrate the use of the reaction plenum for the synthesis of organic molecules in solution. First, the water bath temperature is set at 25° C. using a commercially available temperature controlled (−20° C. to 1500° C.) water circulating bath (model 1140A, VWR Scientific, Plainfield, N.J.) which is connected at the entrance 26 and exit 27 ports (FIG. 5). To a flask containing 0.2 grams (1.2 mmole) 4-aminophenyl acetate (16, Scheme 4) is added using a Tecan liquid handling robot 0.2 grams (1.1 mmoles) of 9-chloroacridine (17, Scheme 4) dissolved in 4 mL of 50% dimethylformamide (DMF) in tetrahydrofuran. To the mixture is then added, using the Tecan liquid handling robot, 1.2 mmoles of diisopropylethylamine (DIEA) and mixture is sonicated at medium power and under nitrogen atmosphere for 5 hours. The crude reaction mixture is then precipitated from water to give crude 9-N-(p-aminophenylacetate)acridine (18) as a sticky oil (Scheme 4).

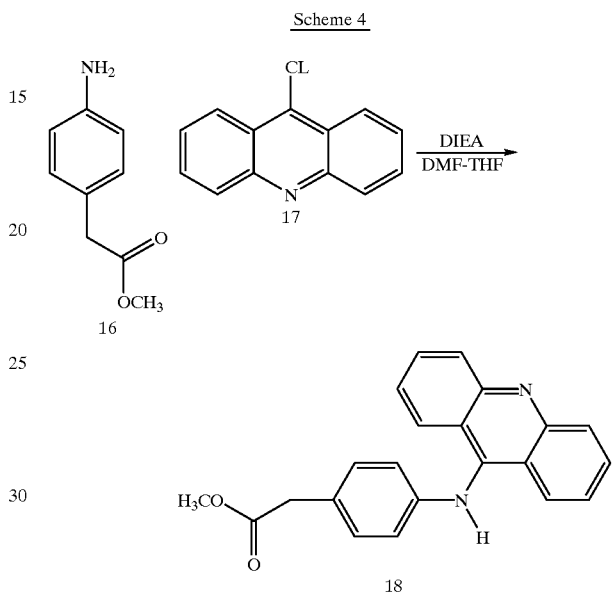

Scheme 4

EXAMPLE 9

Isolation and Purification of DNA From Whole Cells Using Carboxylated Magnetic Beads This example is used to illustrate the use of the reaction plenum for biological applications. To one of the flasks mounted in the reaction plate is added 20 mg (0.1 mmoles/gram) of carboxylated, silica coated paramagnetic beads (obtained from Advanced Magnetics, Cambridge, Mass. To the flask is then added, using the Tecan liquid handling robot, a sample of 0.5 mL of cell suspension (108 cells/ml) in 50 mM Tris.HCl pH 8.0, 10 mM EDTA Buffer. The flask is then sonicated for 5 minutes. To the flask is then added 0.5 mL of a solution composed of 20% polyethylene glycol (MW=8000) in 2.5 M NaCl. The flask is then sonicated for another 5 minutes. The flask is then transferred to the magnetic separation region and the soluble components of the reaction mixture removed by aspiration using the Tecan robot. To the flask is then added 2–3 ml of 5 M NaCl and sonicated on low power for 15 seconds. The flask is then moved to the magnetic separation region and the solvent is removed by aspiration. This process is then repeated two more times. To the flask is then added 1 ml of water and the flask is sonicated for 15 seconds. The particles are then magnetically separated and the water containing the DNA is transferred to another vessel using the Tecan liquid handling robot.

The reaction plates presented in the present invention are primarily designed for solid phase synthesis using paramagnetic particles or for standard solution chemistry. There are currently several commercially available reverse-filtration type reaction blocks such as the Diversomer 8-pin synthesizer produced by Chemglass, Vineland, N.J. and the Combitech reaction block produced by Tecan US, Research Triangle Park, NC that can be used with the present automated reaction plenum. In this case, non-paramagnetic supports are used and the separation of the support is accomplished by reverse filtration. The following example will help demonstrate this application.

EXAMPLE 10

Automated Synthesis of the Non-Peptide Compound 2-N-(p-aminophenylacetate)-5-nitropyridine (10) Using Non-Paramagnetic 2% Cross-Linked Polystyrene a Reverse Filtration Manifold (Scheme 2)

This example is used to demonstrate the use of utility and compatibility of the sonication and water temperature controlled components of the reaction plenum of the present invention and the use of reverse filtration type manifolds.

First, the water bath temperature is set at 25° C. using a commercially available temperature controlled (−20° C. to 150° C.) water circulating bath (model 1140A, VWR Scientific, Plainfield, N.J.) which is connected at the entrance 26 and exit 27 ports (FIG. 5). As shown schematically in FIG. 16, to round bottom flask 50 is added 25 mg of non-paramagnetic resin bound aminophenyl acetate (Scheme 2). The flask is septum stoppered 52 and a glass tube 54 with fritted glass 56 at one of it's ends is pierced through the septum. The fritted glass 56 end of the tube 54 is positioned at the bottom of the round bottom flask (See FIG. 16). Using the liquid handling robot, 27 mg (0.17 mmoles) of 2-chloro-5-nitropyridine dissolved in 1.5 mL of dimethylformamide is syringed into the flask through the septum and mixture sonicated at medium power and at room temperature for 7 hours. One end of a long Teflon tube 58 is attached to the protruding end of the glass fritted tube 54 and the other end is attached to a waste solvent container 60. Enough of a reduced pressure is applied to the waste solvent container 60 to force the liquid from the flask 50, into the glass fritted tube, up through the Teflon tubing and into the waste solvent container. To the flask 50 is then added 2–3 ml of dimethylformamide and sonicated on low power for 30 seconds. A reduced pressure is again applied to the waste container and the dimethylformamide is then removed by suction up the through the fritted glass 56 tube and into the waste container.

This process is then repeated three more times with dimethylformamide and then three times with methanol and then three times with methylene chloride in that order to give resin bound (Scheme 2). To air dried resin (Scheme 2) was added 1 mL of a 0.1 N solution of sodium methoxide in 50% methanol-tetrahydrofuran and mixture sonicated on low power for 5 hours. The liquid was aspirated into another flask and the volatile components of the reaction mixture removed under reduced pressure to give (Scheme 2) as the free base.

Modifications and variations can be made to the disclosed embodiments without departing from the subject and spirit of the invention as defined in the following claims. Such modifications and variations, as included within the scope of these claims, are meant to be considered part of the invention as described.

What is claimed is:

1. Apparatus for performing an organic chemical reaction comprising:

a liquid bath;

at least one reaction vessel arranged to be positioned in said liquid bath;

at least one paramagnetic bead in said at least one reaction vessel;

transporting means for positioning said at least one reaction vessel in said liquid bath;

ultrasonic means external to said reaction vessel for providing an ultrasonic field in said reaction vessel;

computer means for controlling said ultrasonic field;

magnetic field means in said liquid bath for providing a magnetic field; and means for selectively exposing said reaction vessel to said ultrasonic field and to said magnetic field.

2. Apparatus as defined in claim 1 comprising computer means for selectively exposing said at least one reaction vessel.

3. Apparatus as defined in claim 2 wherein the means for selectively exposing includes means for activating and deactivating said ultrasonic means and means for controlling exposure of the magnetic field onto said at least one reaction vessel.

4. Apparatus as defined in claim 1 wherein said means for selectively exposing includes a motor operably connected to a drive mechanism, and a guide mechanism, said drive mechanism operably connected to said means for transporting, said guide mechanism operably connected to said drive mechanism and to said liquid bath.

5. Apparatus as defined in claim 4 wherein said motor is a stepper motor.

6. Apparatus as defined in claim 1 wherein said magnetic field is permanent.

7. Apparatus as defined in claim 6 wherein said magnetic field is provided by at least one neodymium magnetic disc.

8. Apparatus as defined in claim 6 wherein said magnetic field is provided by at least four neodymium magnetic discs arranged polyhedrally proximal to the base of said reaction vessel.

9. Apparatus as defined in claim 8 wherein the base of said at least one reaction vessel is planar and said reaction vessel is comprised of glass.

10. Apparatus as defined in claim 9 wherein said at least one reaction vessel is conical.

11. Apparatus as defined in claim 1 wherein the magnetic field is inducible.

12. Apparatus as defined in claim 1 wherein said means for providing said ultrasonic field is an ultrasonic transducer of the probe type.

13. Apparatus as defined in claim 1 wherein said means for providing said ultrasonic field is an ultrasonic transducer of the bath type.

14. Apparatus as defined in claim 1 wherein said liquid is water.

15. Apparatus for performing an organic chemical reaction comprising:

a liquid bath;

at least one reaction vessel arranged to be positioned in said liquid bath;

at least one paramagnetic bead in said at least one reaction vessel;

dispensing means for dispensing a solvent into said at least one reaction vessel;

transporting means for positioning said at least one reaction vessel in said liquid bath;

ultrasonic means external to said reaction vessel for providing an ultrasonic field in said reaction vessel;

magnetic field means in said liquid bath for providing a magnetic field; and means for selectively exposing said reaction vessel to said ultrasonic field and to said magnetic field.

16. Apparatus as defined in claim 15 comprising aspirating means for aspirating said solvent.

17. Apparatus as defined in claim 16 comprising computer means for controlling said dispensing means and said aspirating means.

18. Apparatus as defined in claim 17 wherein said computer means includes at least one liquid handling robot.

19. Apparatus for performing an organic chemical reaction comprising:

a liquid bath;

at least one reaction vessel arranged to be positioned in said liquid bath;

at least one paramagnetic bead in said at least one reaction vessel;

transporting means for positioning said at least one reaction vessel in said liquid bath;

said transporting means includes supply means for supplying an inert atmosphere to said reaction vessel;

ultrasonic means external to said reaction vessel for providing an ultrasonic field in said reaction vessel;

magnetic field means in said liquid bath for providing a magnetic field; and means for selectively exposing said reaction vessel to said ultrasonic field and to said magnetic field.

20. Apparatus as defined in claim 19 wherein said transporting means positions said at least one reaction vessel at a preselected depth and includes an inner compartment which is operably connected to said at least one reaction vessel, and further comprising means for maintaining a dry and inert atmosphere with a positive pressure including an inlet and outlet port which allows an inert atmosphere to circulate within said at least one reaction vessel and said inner compartment.

21. Apparatus for performing an organic chemical reaction comprising:

a liquid bath;

temperature control means for regulating the temperature of said liquid;

at least one reaction vessel arranged to be positioned in said liquid bath;

at least one paramagnetic bead in said at least one reaction vessel;

transporting means for positioning said at least one reaction vessel in said liquid bath;

ultrasonic means external to said reaction vessel for providing an ultrasonic field in said reaction vessel;

magnetic field means in said liquid bath for providing a magnetic field; and means for selectively exposing said reaction vessel to said ultrasonic field and to said magnetic field.

22. Apparatus as defined in claim 21 wherein said temperature control means is computer controlled.

23. Apparatus as defined in claim 22 wherein said ultrasonic transducer is a 600 Watt 25 kHz immersible ultrasonic transducer.

24. Apparatus as defined in claim 22 wherein said ultrasonic transducer is a 600 Watt 40 kHz immersible ultrasonic transducer.

25. Apparatus for performing an organic chemical reaction in a plurality of reaction vessels positioned in a liquid bath, at least one of said reaction vessels provided with at least one non-paramagnetic bead, said apparatus comprising:

a liquid bath;

a plurality of reaction vessels positioned within said liquid bath;

a reverse filtration system operably associated with said reaction vessels, said reverse filtration system separating solids from liquids within each of said plurality of said reaction vessels;

ultrasonic means located in said liquid bath external to said reaction vessels for substantially simultaneously providing an ultrasonic field in all of said reaction vessels; and means for controlling the ultrasonic means by actuating and deactuating the ultrasonic means and for controlling the amplitude and duration of the ultrasonic field of said ultrasonic means to produce a field across said plurality of reaction vessels.

26. Apparatus as defined in claim 25 wherein said liquid is water.

27. Apparatus for performing an organic chemical reaction in a plurality of reaction vessels positioned in a liquid bath, said reaction vessels provided with a starting material dissolved in an organic solvent, said apparatus comprising:

a liquid bath;

a plurality of reaction vessels positioned within said liquid bath;

ultrasonic means located in said liquid bath external to said reaction vessels for substantially simultaneously providing a substantially uniform ultrasonic field in all of said plurality of said reaction vessels;

said ultrasonic means having an ultrasonic emitting surface area underlying all of said plurality of said reaction vessels; and means for controlling the ultrasonic means by actuating and deactuating the ultrasonic means and for controlling the amplitude and duration of the ultrasonic field of said ultrasonic means to produce a substantially uniform field across said plurality of reaction vessels.

28. Apparatus as defined in claim 27 wherein said liquid is water.

29. Apparatus for performing an organic chemical reaction comprising:

a liquid bath;

a plurality of reaction vessels arranged to be positioned in said liquid bath;

at least one paramagnetic bead in at least one of said reaction vessels;

transporting means operably connected to said reaction vessels for positioning said reaction vessels in said liquid bath;

ultrasonic means external to said reaction vessels for providing an ultrasonic field in said reaction vessels;

magnetic field means in said liquid bath for providing a magnetic field; and means for selectively exposing said reaction vessels to said ultrasonic field and to said magnetic field.

30. Apparatus as defined in claim 29 wherein said magnetic field is permanent.

31. Apparatus as defined in claim 30 wherein said magnetic field is provided by at least one neodymium magnetic disc.

32. Apparatus as defined in claim 29 further comprising temperature control means for regulating the temperature of said liquid.

* * * * *